(12) United States Patent
Hall et al.

(10) Patent No.: US 10,969,365 B2
(45) Date of Patent: Apr. 6, 2021

(54) NANOPORE ANALYSIS OF GLYCOSAMINOGLYCAN COMPOSITIONS

(71) Applicants: Wake Forest University Health Sciences, Winston-Salem, NC (US); University of Oklahoma Health Sciences Center, Oklahoma City, OK (US)

(72) Inventors: Adam R. Hall, Clemmons, NC (US); Elaheh Rahbar, Winston-Salem, NC (US); Paul DeAngelis, Edmond, OK (US)

(73) Assignees: WAKE FOREST UNIVERSITY HEALTH SCIENCES, Winston-Salem, NC (US); THE BOARD OF REGENTS OF THE UNIVERSITY OF OKLAHOMA, Norman, OK (US)

(*) Notice: Subject to any disclaimer, the term of this patent is extended or adjusted under 35 U.S.C. 154(b) by 24 days.

(21) Appl. No.: 16/276,209

(22) Filed: Feb. 14, 2019

(65) Prior Publication Data

US 2019/0250126 A1 Aug. 15, 2019

Related U.S. Application Data

(60) Provisional application No. 62/630,601, filed on Feb. 14, 2018.

(51) Int. Cl.
*G01N 27/327* (2006.01)
*G01N 27/447* (2006.01)
*G01N 33/487* (2006.01)

(52) U.S. Cl.
CPC . *G01N 27/44791* (2013.01); *G01N 33/48721* (2013.01)

(58) Field of Classification Search
None
See application file for complete search history.

(56) References Cited

U.S. PATENT DOCUMENTS 5,416,071 A * 5/1995 Igari .................. A61K 38/1816
514/21.92
2019/0256616 A1* 8/2019 Zhang ..................... G16B 40/10

OTHER PUBLICATIONS

Masters Thesis by Felipe Rivas Duarte entitled, "Molecular Analysis of Hyaluronic Acid (HA) Using Solid-State Nanopores," presented Aug. 2017, Virginia Tech-Wake Forest School of Biomedical Engineering (Year: 2017).*
U.S. Appl. No. 62/571,077, filed Oct. 11, 2017.*
Fennouri et al., "Single Molecule Detection of Glycosaminoglycan Hyaluronic Acid Oligosaccharides and Depolymerization Enzyme Activity Using a Protein Nanopore," ACSNano vol. 6, No. 11, pp. 9672-9678, 2012 (Year: 2012).*

* cited by examiner

*Primary Examiner* — Alexander S Noguerola
(74) *Attorney, Agent, or Firm* — J. Clinton Wimbish; Nexsen Pruet, PLLC

(57) ABSTRACT

In one aspect, methods of biomolecular analysis are described herein. Briefly, a method comprises providing a composition comprising glycosaminoglycans and contacting the composition with a membrane comprising at least one nanopore. An electric field is applied across the nanopore, and data of glycosaminoglycan translocation events through the nanopore are recorded. A molecular weight distribution of the glycosaminoglycans is derived from the data.

4 Claims, 18 Drawing Sheets

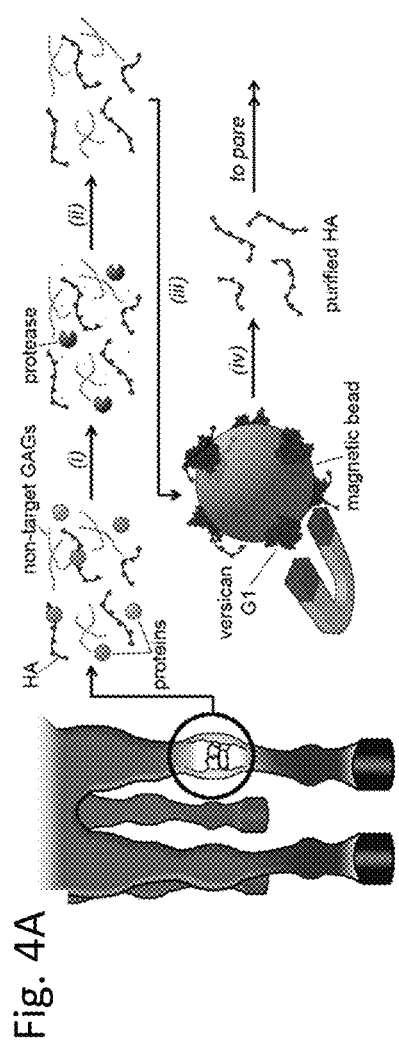
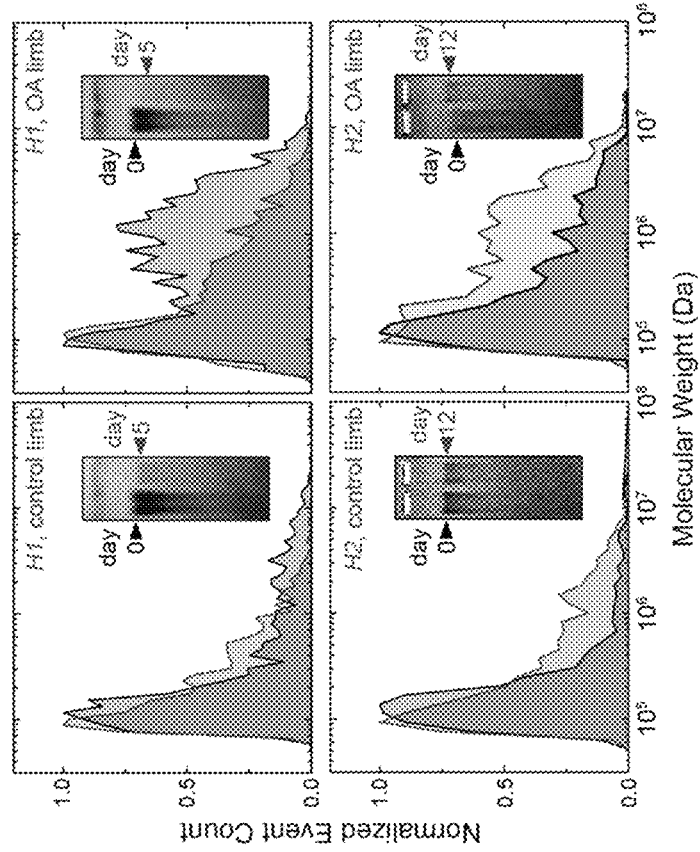
Fig. 4A
Fig. 4B
Fig. 4C
Fig. 4D
Fig. 4E

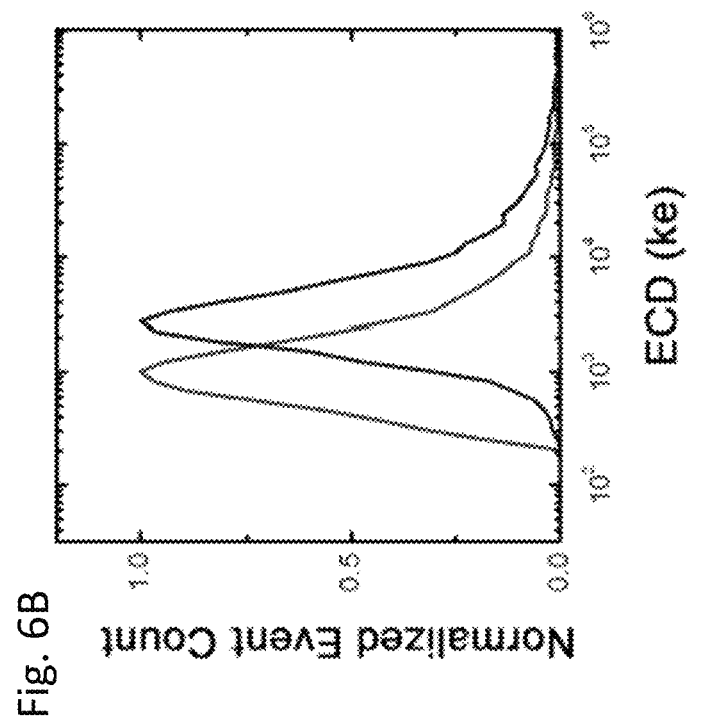
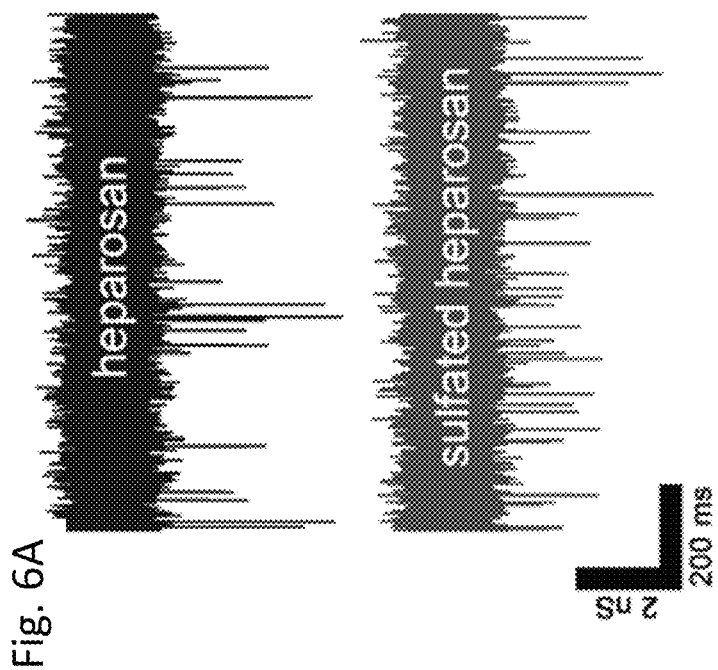
Fig. 6A
Fig. 6B

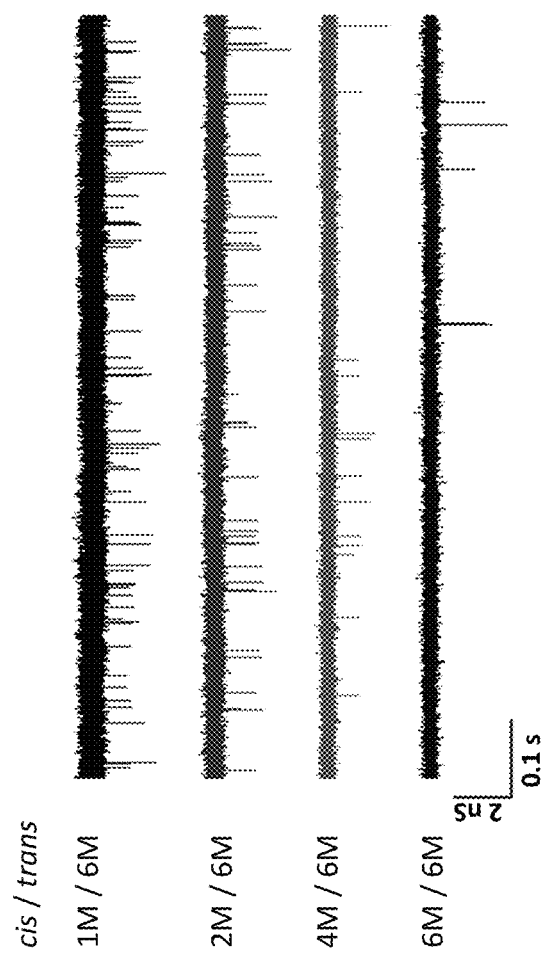

NANOPORE ANALYSIS OF GLYCOSAMINOGLYCAN COMPOSITIONS

CROSS-REFERENCE TO RELATED APPLICATIONS

This application claims priority pursuant to 35 U.S.C. § 119 to U.S. Provisional Patent Application No. 62/630,601, filed on Feb. 14, 2018, which is hereby incorporated by reference in its entirety.

FIELD

The present invention relates to the analysis of biomolecular compositions with solid state nanopore architectures and, in particular, to nanopore analysis and characterization of glycosaminoglycan compositions.

BACKGROUND

Glycosaminoglycans (GAGs) are linear polysaccharides found ubiquitously throughout the body, where they regulate numerous physiologic and pathologic processes. Their diverse biological functions are highly dependent on structure; as a result, a variety of GAGs exist, each featuring distinct size ranges and an assortment of chemical modifications influencing their binding and/or signaling capacity.

Structural heterogeneity and chemical variations of glycans, including GAGs, have made the development of robust analytical techniques to probe glycans and glycan-protein interactions challenging, ultimately hindering growth in the glycosciences and in diagnostics. Current methods to quantify glycan size and abundance (e.g., mass spectrometry, gel electrophoresis, chromatography, etc.) tend to be expensive, cumbersome, and/or require large sample masses/volumes. Most technologies also require specialized equipment and expertise, limiting their accessibility to the field. In summary, no truly "user-friendly" method exists to study, measure or detect most glycoconjugates or carbohydrate-binding proteins. Thus, there is a need to develop translational tools and methods that can reliably probe key glycans and glycan-protein interactions and levels. For maximum impact and widespread dissemination, these tools should be easy to use, yield uncomplicated results, and be affordable.

SUMMARY

In one aspect, methods of biomolecular analysis are described herein. Briefly, a method comprises providing a composition comprising glycosaminoglycans and contacting the composition with a membrane comprising at least one nanopore. An electric field is applied across the nanopore, and data of glycosaminoglycan translocation events through the nanopore are recorded. A molecular weight distribution of the glycosaminoglycans is derived from the data. In some embodiments, the data comprises dwell time of the glycosaminoglycans in the nanopore. Data can also comprise translocation event depth of the glycosaminoglycans. The resultant molecular weight distribution can comprise glycosaminoglycans having molecular weight less than 500 kDa and/or glycosaminoglycans having molecular weight of 500 kDa or greater. Moreover, any desired molecular weight threshold can be assigned to the distribution to characterize one or more properties of the glycosaminoglycans. The molecular weight distribution can be employed in various applications. The molecular weight distribution, for example, can be used in quality control analysis of pharmaceutical compositions comprising glycosaminoglycans. The molecular weight distribution may also be used in the diagnosis, evaluation and/or monitoring of a disease or a normal biological function. For example, the molecular weight distribution can be used in one or more components or steps of disease management including detection, stratification, choice of intervention and/or monitoring response to the intervention. In such embodiments, the composition comprising the glycosaminoglycans can be collected from a biological source including, but not limited to, a human, animal, plant and/or microorganism. If required, the composition can be purified (e.g. via differential separations, on-line extraction) to isolate the glycosaminoglycans prior to nanopore analysis. In some embodiments, the composition comprising the glycosaminoglycans can be collected from an artificial system, such as bioengineered constructs. If required, the composition from the artificial system can be purified to isolate the glycosaminoglycans prior to nanopore analysis. Additionally, the number of events in the data can be used to derive concentration of level of the glycosaminoglycans.

In another aspect, a method of biomolecular analysis comprises providing a mixture comprising sulfated glycosaminoglycans and contacting the mixture with a membrane comprising at least one nanopore. An electric field is applied across the nanopore, and data of glycosaminoglycan translocation events through the nanopore are recorded. Sulfated glycosaminoglycans are differentiated with the data according to an amount of sulfation. In some embodiments, the data comprises dwell time of the sulfated and non-sulfated glycosaminoglycans in the nanopore. The data may also comprise translocation event depth of the sulfated and non-sulfated glycosaminoglycans.

In a further aspect, a method of biomolecular analysis comprises providing a mixture comprising glycosaminoglycans and proteins and contacting the mixture with a membrane comprising at least one nanopore. An electric field is applied across the nanopore, and data of biomolecular translocation events through the nanopore are recorded. Interactions between glycosaminoglycans and proteins are derived from the data. Interactions can include glycosaminoglycan-protein binding. In some embodiments, the data comprises dwell time of glycosaminoglycan-protein complexes in the nanopore and/or translocation event depth of the glycosaminoglycan-protein complexes. The data may also comprise translocation event depth of the glycosaminoglycan chains with a bound molecule such as a protein or peptide with a larger molecular weight or diameter when compared to the free sugar chain alone.

These and other embodiments are described in greater detail in the detailed description which follows.

BRIEF DESCRIPTION OF THE DRAWINGS

FIG. 4A is an illustration of an HA isolation protocol: (step i) collected equine synovial fluid is treated with a broad-spectrum protease to digest proteins; (step ii) liquid-liquid phase extraction is used to remove protease and remnant protein components; (step iii) HA is selectively isolated on versican G1 magnetic beads; and (step iv) elution yields pure HA for SS-nanopore analysis.

FIGS. 4B-4E illustrates equine synovial fluid HA size distributions obtained from SS-nanopore ECD analysis by comparison to a calibration curve, as in FIG. 3D. For each, day 0 is represented by a black line and day 5 or 12 is represented by a gray line. Horse H1 control (sham knee): day 0 (n=1768), day 5 (n=1680); H1 induced OA knee: day 0 (n=2590), day 5 (n=2849); H2 control (sham knee): day 0 (n=1748), day 12 (n=1692); H2 induced OA knee: day 0 (n=1141), day 12 (n=1215). Insets show accompanying gel images for the same synovial fluid samples with band positions marked.

FIG. 6A illustrates conductance traces (symmetric 6 M LiCl) showing translocations of unsulfated (black) and 6-O-sulfated heparosan (gray), demonstrating high signal-to-noise ratio (SNR) analysis of these GAGs. Both synthetic glycans have ~95 kDa backbones (~470 sugars).

FIG. 6B illustrates normalized ECD distributions for the molecular species of FIG. 6A. The shift suggests a direct correlation between signal and sulfation.

FIG. 14A illustrates an exemplary SS-nanopore conductance trace for 3 ng/uL concentration polydisperse HA under symmetric or asymmetric salt measurements of either 1 M:6 M, 2 M:6 M, 4 M: 6M, or 6 M:6 M (cis:trans) salt concentrations.

DETAILED DESCRIPTION

Figure 1B:
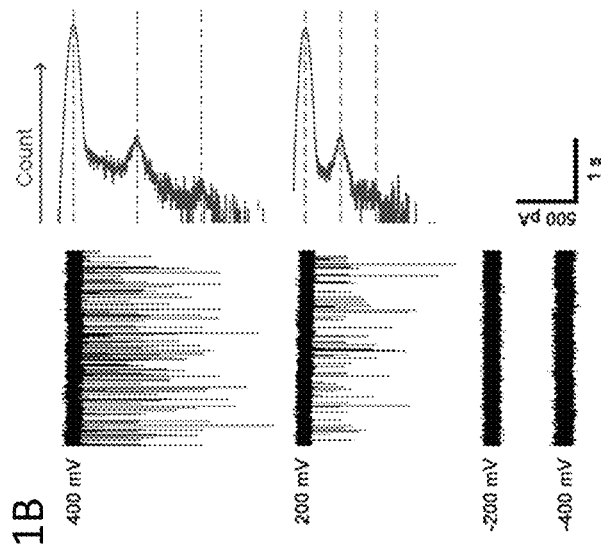
FIG. 1B illustrates raw current traces obtained from a 6.5 nm SS-nanopore with HA introduced on one electrically-grounded chamber (cis-) and indicated voltage applied to the other chamber (trans-). Events were observed only toward positive bias. All-points histograms (red) show quantized current levels (dashed lines), indicating molecular folding.

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

In one aspect, methods of biomolecular analysis are described herein, which in some embodiments comprises (i) providing a composition comprising glycosaminoglycans; (ii) contacting the composition with a membrane comprising at least one nanopore; (iii) applying an electric field across the nanopore; (iv) recording data of glycosaminoglycan translocation events through the at least one nanopore; and (v) deriving a molecular weight distribution of the glycosaminoglycans from the data.

In some embodiments, data recorded while applying an electric field across the nanopore can comprise one or more measurements related to a measured transmembrane ionic current across the nanopore as a biomolecule, such as a glycosaminoglycan, translocates through the nanopore. For example, in some embodiments the data can comprise a dwell time of the glycosaminoglycans in the nanopore. A dwell time, as understood by one of ordinary skill in the art, refers to a measurement of time corresponding to the amount of time required for a biomolecule, such as a glycosaminoglycan, to translocate through a nanopore. That is, the dwell time is a measure of how long the transmembrane ionic current across the nanopore is disrupted or reduced when a biomolecule passes through the nanopore.

In some embodiments, data recorded while applying an electric field across the nanopore can comprise a translocation event depth. A translocation event depth, as understood by one of ordinary skill in the art, refers to a measurement corresponding to an amount of current or conductance change, averaged across a dwell time, as defined above, and caused by a translocating biomolecule entering the nanopore from a first chamber and exiting the nanopore into a second chamber during a translocation event. That is, in a trace of measured current or conductance across the nanopore, the translocation event depth is a current or conductance measured on a y-axis, whereas the dwell time is a time measured on an x-axis from the beginning of the translocation event to the end of the translocation event when the current or conductance returns to a baseline value.

In some embodiments, data recorded while applying an electric field across the nanopore can comprise a rate of translocation events. A rate of translocation events can be calculated or determined by counting a quantity of translocation events per a unit of time. For example, a rate of translocation events can be measured as a number of events per second. Additionally, a rate of translocation events can be calculated or determined by counting a quantity of translocation events per a unit of time at a certain applied voltage. For example, a rate of translocation events can be measured as a number of events per second per mV applied voltage.

As understood by one of ordinary skill in the art, a dwell time, a translocation event depth, and a rate of translocation events are each distinct metrics that are not interchangeable and characterize a specific attribute or feature of the methods described herein. In some embodiments, recording data while applying an electric field across the nanopore can comprise recording a conductance trace, and the conductance trace can comprise data including, but not limited to, dwell time, translocation event depth, and rate of translocation events.

In some embodiments, a method described herein comprises deriving a molecular weight distribution of the glycosaminoglycans from the recorded data. In some embodiments, deriving a molecular weight distribution of the glycosaminoglycans from the recorded data can comprise deriving a molecular weight distribution of the glycosaminoglycans from a conductance trace, including from a dwell time, a translocation event depth, a rate of translocation events, or any one or combination thereof.

In some cases, deriving a molecular weight distribution of the glycosaminoglycans from the recorded data can comprise quantifying a plurality of amounts of glycosaminoglycans of one or more molecular weight ranges and/or determining or calculating a mean or an average molecular weight of a plurality of amounts of glycosaminoglycans. For example, in some cases, a molecular weight distribution can comprise a plurality of amounts of glycosaminoglycans of one or more molecular weights. In some cases, the molecular weight distribution can comprise glycosaminoglycans having molecular weight less than 500 kDa and/or glycosaminoglycans having molecular weight greater than 500 kDa. In some cases, the molecular weight distribution can comprise a profile of glycosaminoglycans, wherein the profile represents a plurality of amounts of glycosaminoglycans of one or more molecular weights. For example, in some instances, a profile can comprise a plurality of amounts of glycosaminoglycans above or below a certain molecular weight threshold. In some instances, such a threshold can be above or below 100 kDa, 200 kDa, 300 kDa, 500 kDa, 600 kDa, 700 kDa, 800 kDa, 900 kDa, 1000 kDa, 1100 kDa, 1200 kDa, 1300 kDa, 1400 kDa, 1500 kDa, 1600 kDa, 1700 kDa, 1800 kDa, 1900 kDa, 2000 kDa, 2100 kDa, 2200 kDa, 2300 kDa, 2400 kDa, 2500 kDa, 2600 kDa, 2700 kDa, 2800 kDa, 2900 kDa, or 3000 kDa. In some cases, a profile can comprise a plurality of amounts of glycosaminoglycans within one or more ranges of molecular weight. In some instances such a range can include any range or subrange between 10 kDa and 5000 kDa.

In some embodiments, a method described herein comprises providing a composition comprising glycosaminoglycans. The composition, in some cases, can be a pharmaceutical composition. For example, a pharmaceutical composition comprising glycosaminoglycans can comprise synthetic or naturally occurring glycosaminoglycans. A synthetic glycosaminoglycan can include any glycosaminoglycan produced by an artificially induced synthesis of glycosaminoglycan, such as from a genetically engineered or viral infected eukaryotic or prokaryotic cell, or an engineered animal, plant, fungal or bacterial system. A naturally occurring glycosaminoglycan can include any glycosaminoglycan extracted from a living organism naturally synthesizing glycosaminoglycans. In some cases, the pharmaceutical composition can be an intra-articular formulation. For example, an intra-articular formulation can comprise hyaluronic acid. The hyaluronic acid of an intra-articular formulation, in some instances, can have a molecular weight of 500 kDa or more.

In some embodiments, a method described herein further comprises comparing the molecular weight distribution to a glycosaminoglycan molecular weight threshold. For example, in some instances, it is desirable for a composition to comprise a certain profile of glycosaminoglycan, as described above. Therefore, in some instances, the molecular weight distribution can be compared to a profile of glycosaminoglycan, as described above. In some embodiments, the composition of a method can comprise a composition collected from a biological source. For example, the composition can be collected from a human, animal, plant, microorganism, or bioengineered construct. In some cases, the composition can comprise a tissue sample or a bodily fluid, such as sweat, cerebral spinal fluid, synovial fluid, urine, bronchial lavage, saliva, tears, vitreous humor, blood, or plasma. Other bodily fluids can also be used.

In some embodiments, a method described herein further comprises purifying the composition to isolate the glycosaminoglycans. Purifying, in some cases, can comprises one or more purification steps, and in some cases, a purification step can use a commercially purchased purification kit. For example, in some instances, depending on the source of the composition, purification can include one or more enzymatic digestion, phenol extraction, chloroform extraction, or immunoprecipitation steps. In some embodiments, purifying the composition can comprise dialyzing the composition to minimize or reduce a native or natural salt concentration of the composition. In some cases, purifying the composition can comprise narrowing the type or types of glycosaminoglycan present in the composition. For example, in some instances, the glycosaminoglycans of a composition described herein can comprise carboxylated and/or sulfated glycosaminoglycans. For example, in some cases, the glycosaminoglycans can be hyaluronic acid, chondroitin sulfate, keratin sulfate, dermatan sulfate, heparin, heparan sulfate, heparosan, sulfated heparosan, or any derivative and/or mixture thereof. Thus, purifying the composition, in some cases, can comprise purifying to isolate or select one or more types of glycosaminoglycan or a class of glycosaminoglycan, as described above. For example, in some embodiments, purifying the composition can comprise purifying sulfated glycosaminoglycans and/or non-sulfated glycosaminoglycans.

In some embodiments, the molecular weight distribution can be employed in the diagnosis, evaluation, and/or monitoring of a disease. In some cases, the composition is derived from a patient. For example, a method described herein can comprise deriving a molecular weight distribution to diagnose, evaluate, and/or monitor a disease, for example a disease of a patient. The molecular weight distribution can be derived, for example, before and/or after administration of a treatment to the patient. In some embodiments, the disease can be a musculoskeletal, metabolic, or cardiovascular disease. For example, a disease, in some instances can be osteoarthritis, metabolic syndrome or metabolic disorder, trauma endotheliopathy, an inflammatory disorder, a cardiovascular disease, an arthritis, or a cancer.

In some embodiments, the molecular weight distribution can be employed to monitor normal biological function of a system. For example, a method described herein can comprise deriving a molecular weight distribution to evaluate, based on known values understood by one of ordinary skill in the art, a distribution of glycosaminoglycans or a profile of glycosaminoglycans in a biological system.

In another aspect, a method of biomolecular analysis is described herein, which in some embodiments, comprises (i) providing a mixture comprising sulfated glycosaminoglycans and, optionally, non-sulfated glycosaminoglycans; (ii) contacting the mixture with a membrane comprising at least one nanopore; (iii) applying an electric field across the nanopore; (iv) recording data of glycosaminoglycan translocation events through the at least one nanopore; and (v) differentiating the sulfated glycosaminoglycans with the data according to an amount of sulfation. In some cases, a method of biomolecular analysis comprises differentiating the sulfated glycosaminoglycans from the data. In some cases, a method of biomolecular analysis comprises differentiating the sulfated glycosaminoglycans from non-sulfated glycosaminoglycans from the data.

In some cases, differentiating the sulfated glycosaminoglycans can comprise determining an amount, level, degree, or quantity of sulfation of the sulfated glycosaminoglycans in the mixture. For example, a mixture comprising sulfated glycosaminoglycans can comprise a plurality of glycosaminoglycans and the plurality of glycosaminoglycan can comprise varying amounts or levels of sulfation. In some embodiments, the amount of sulfation of a glycosaminoglycan can be differentiated according to a charge density or a charge per unit of length of the sulfated glycosaminoglycan. In some embodiments, the charge density or charge per unit of length of a sulfated glycosaminoglycan can be determined or quantified relative to other glycosaminoglycans in the mixture. For example, in some instances, the varying or differing amounts of sulfation can be a relative difference to other glycosaminoglycans present in the mixture, e.g. a 1×, 2×, 3×, or n× difference, wherein n is any number representing a multiplier of the change in the amount of sulfation. In some embodiments, the charge density or charge per unit of length of a sulfated glycosaminoglycan can be determined or quantified directly from the recorded data. For example, in some instances, the varying or differing amounts of sulfation can be determined from the recorded data.

In some embodiments, recording data of glycosaminoglycan translocation events can comprise recording a conductance trace, as described above. For example, the data, in some cases, can comprise dwell time of the sulfated and/or non-sulfated glycosaminoglycans in the nanopore. In some instances, the data can comprise translocation event depth of the sulfated and/or non-sulfated glycosaminoglycans. In some embodiments, the data can comprise dwell time and translocation event depth of the sulfated and/or non-sulfated glycosaminoglycans. In some embodiments, the mixture comprising the sulfated and/or non-sulfated glycosaminoglycans can be collected from a human, animal, plant, microorganism or bioengineered construct, as described above. For example, in some cases, the mixture can comprise synthetic and/or natural glycosaminoglycans. In some embodiments, the mixture can be a pharmaceutical composition.

In another aspect, a method of biomolecular analysis is described herein, which in some embodiments comprises (i) providing a mixture comprising glycosaminoglycans and proteins; (ii) contacting the mixture with a membrane comprising at least one nanopore; (iii) applying an electric field across the nanopore; (iv) recording data of biomolecular translocation events through the nanopore; and (v) deriving glycosaminoglycan-protein interactions from the data. In some embodiments, the glycosaminoglycan-protein interactions can include glycosaminoglycan-protein binding, which can include binding via covalent bonding, ionic bonding, hydrogen bonding, Van der Waal forces, or any combination thereof.

In some embodiments, recording data of biomolecular translocation events through the nanopore can comprise recording a conductance trace, as described above. For example, the data in some cases, can comprise dwell time of glycosaminoglycan-protein complexes in the nanopore. In some instances, the data can comprise translocation event depth of glycosaminoglycan-protein complexes in the nanopore. In some embodiments, the data can comprise dwell time and translocation event depth of glycosaminoglycan-protein complexes in the nanopore. In some embodiments, the mixture comprising the glycosaminoglycans and proteins can be collected from a human, animal, plant, microorganism or bioengineered construct, as described above.

Various implementations of methods have been described, and exemplary embodiments are described below in fulfillment of various objectives of this disclosure. It should be recognized that these implementations are merely illustrative of the principles of this disclosure. Numerous modifications and adaptations thereof will be readily apparent to those skilled in the art without departing from the spirit and scope of this disclosure. For example, individual steps of methods described herein can be carried out in any manner not inconsistent with the objectives of this disclosure, and various configurations or adaptations of devices described herein may be used in such methods.

EXAMPLE 1

SS-Nanopore-Based Detection of HA

Figure 1A:
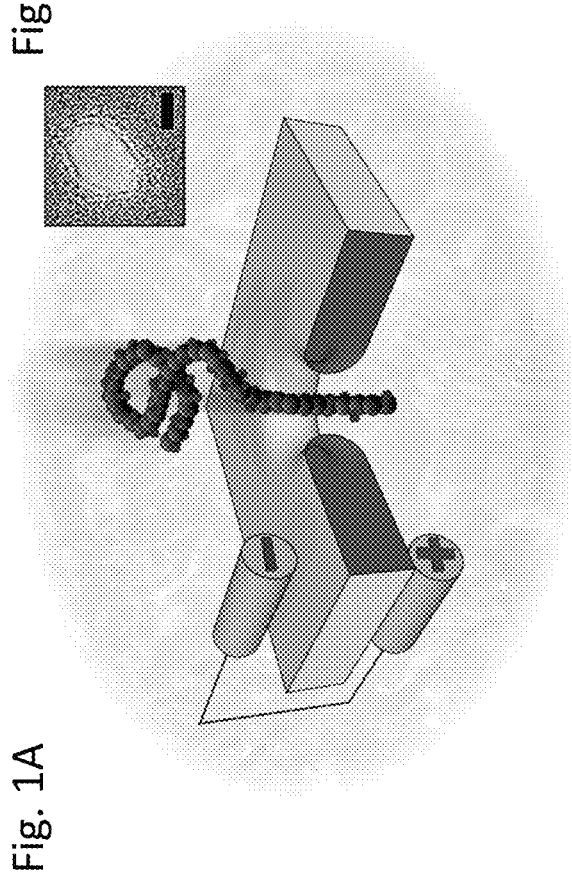
FIG. 1A is a schematic representation of electrophoretic translocation of HA through a SS-nanopore. Inset: transmission electromicrograph of a typical SS-nanopore fabricated with the same procedure used here. Scale bar, 5 nm.

Here, a new HA analysis approach based on solid-state (SS-) nanopores is described, an emerging platform for sensitive molecular analysis. The system uses a nanometer-scale aperture in a thin membrane (FIG. 1a, inset), positioned as the only fluid connection between two reservoirs of an electrolyte solution. An applied voltage is used to generate a strong electric field inside the opening that impels charged molecules electrophoretically through it and into the opposing chamber (FIG. 1a). During their residence inside the pore, each molecule occupies space that would otherwise be occupied by ions contributing to the electrical signal, and so their passage is marked by a temporary reduction (an "event") in the measured transmembrane ionic current. The concept of resistive pulse sensing was first applied to HA by Fennouri, et al, using the aerolysin protein pore. However, only small HA (<10 individual sugar residues) could be measured with that system. In methods described herein, fabricated SS-nanopores are exploited to probe HA polysaccharides. The flexibility of this platform enables both detection and MW discrimination across a broad range of molecular sizes and its speed and quantitative output suggest a direct route to translational applications.

EXAMPLE 2

SS-Nanopore Measurement of Polydisperse HA

As an initial assessment of the utility of SS-nanopores to probe HA, a first set of experiments was conducted using a polydisperse mixture of HA isolated from *Streptococcus zooepidemicus* fermentation, having a broad range of MW. The resulting current traces (FIG. 1b) confirmed the ability of SS-nanopores to resolve HA easily, typically yielding events that were at least five standard deviations ($5\sigma$) above the noise floor. As negatively charged molecules, HA was observed to move only towards the positive bias, indicating that their translocations were governed predominantly by electrophoresis. Additionally, by reversing the applied bias after a measurement, recaptured HA events were measured, confirming that the molecules fully translocated through the pore. Turning to event characteristics, integral variation was noted in the measured translocation event depth histograms (FIG. 1b, right) that were suggestive of stochastic variations in molecular folding conformation during threading, similar to past measurements with DNA. While event durations have typically been more correlated with MW than depth in previous reports, signal variations of this kind can skew the data, since folded molecules translocate more rapidly than unfolded ones. Consequently, analyses described herein utilized the experimental factor of event charge deficit (ECD). The ECD value comprises both the event depth, i.e. the translocation event depth, and the event duration, i.e. the dwell time, by considering the integrated area of each event, thereby normalizing differences in molecular conformation and yielding lower ECD for smaller molecular sizes. A typical polydisperse HA ECD histogram (FIG. 1c) showed a Gaussian distribution spanning over four orders of magnitude. This wide population was indicative of the broad MW distribution within the sample.

Figure 1E:
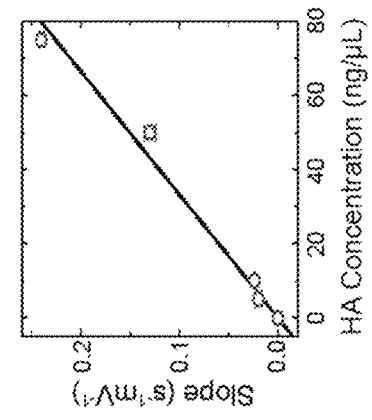
FIG. 1E illustrates the slopes from FIG. 1D showing a linear dependence (solid line) on net HA concentration.
Figure 1D:
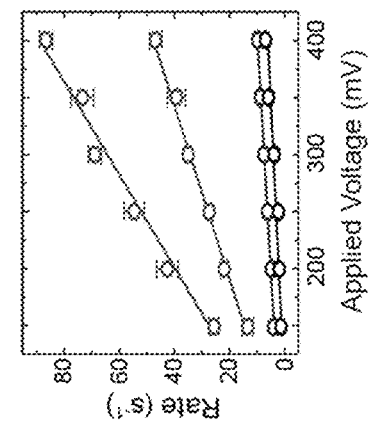
FIG. 1D illustrates a voltage-dependent event rate for three concentrations of polydisperse HA (top-bottom: 75, 50, 10, and 5 ng/μl). Solid lines are linear fits to the data points.

Further probing the translocation dynamics of polydisperse HA through SS-nanopores, the dependence of molecular capture rate on both applied voltage and net sample concentration was measured. (FIG. 1d). For all measured conditions, a linear relationship was observed between voltage and event rate, indicating a diffusion-limited translocation regime and suggesting that there was no significant energetic barrier related to entry of HA into the confined space of the nanopore for the system. Another consequence of diffusion-limited kinetics is an absence of size dependence in the event rate, enabling an unbiased representation of MW distribution in the SS-nanopore signal. That is, in a diffusion-limited translocation regime a small or low MW glycosaminoglycan has an equal probability of translocating through a nanopore as a large or high MW glycosaminoglycan at any given point in time during an applied voltage bias across the nanopore, provided an equivalent charge density or charge per unit length of the glycosaminoglycans. Accordingly, there was no observed difference in the translocation event rate of small versus large glycosaminoglycans. It was also observed that overall event rates were strongly impacted by the net concentration of polydisperse HA in solution. Measurements yielded a linear response in recorded event rate dependence (slope) between 5 and 75 ng/µl (FIG. 1e). Featuring an intercept at 0, this result suggested that arbitrarily low concentrations could in principle be probed with a concomitant reduction in measured event rate. Furthermore, translocations could also be detected above 75 ng/µl, but often caused clogging at high applied voltages and were therefore not included here. Accordingly, FIG. 1D and FIG. 1E illustrate that the present nanopore system can calculate or determine a net concentration of glycosaminoglycan based on a rate of translocation events. Taken as a whole, this predictable variation indicated a route toward direct quantification of total HA with SS-nanopores, similar to previous studies on nucleic acids and nucleoprotein-protein complexes. In the present Example, and others, purified polydisperse HA was prepared as described below, and SS-nanopore preparation and SS-nanopore analysis of HA were performed as described below.

HA Samples

Purified polydisperse *Streptococcus zooepidemicus* HA (Vesta, Indianapolis, Ind.) was mixed as received in deionized water to a concentration of 1 µg/µl as a bulk solution. No further purification was performed. Discrete quasi-monodisperse HA samples were provided by Hyalose, Inc. (Oklahoma City, Okla.). A total of seven quasi-monodisperse HA samples (54, 81, 130, 237, 545, 1076, and 2384 kDa) were used, with MW within 5% of the reported mean (polydispersity=1.001-1.035, as estimated by MALLS- SEC). Each 50 μg lyophilized sample was mixed with deionized water to produce a 1 μg/μl solution. All samples were stored in LoBind eppendorf tubes (Fisher Scientific, Hampton, N.H.) at 4° C. for short term use, or kept at −20° C. for long-term storage.

SS-Nanopore Preparation

Silicon chips (4 mm) with a thin, free-standing silicon nitride membrane (8-20 μm with 20-25 nm thickness) were obtained commercially (Norcada, Inc. Alberta, Canada) for solid-state nanopore fabrication. Individual pores were formed in house using an Orion Plus helium ion microscope (Carl Zeiss, Peabody, Mass.) following methods described elsewhere. All nanopores used in this work were produced with diameters in the range of 6-8 nm, unless otherwise indicated. Following fabrication, chips were stored in 50% ethanol solution prior to use. In preparation for measurement, each nanopore chip was rinsed with DI water and absolute ethanol, then dried with filtered air, and subsequently exposed to a 30 W air plasma (Harrick Plasma, Ithaca, N.Y.) for two minutes on each side before being positioned in a custom Ultem 1000 flow cell. Measurement buffer (6 M LiCl, 10 mM Tris, 1 mM EDTA, pH 8.0) was then introduced to both sides of the chip and Ag/AgCl electrodes (Sigma-Aldrich, St. Louis, Mo.) positioned in each chamber for voltage application and ionic current measurement using an Axopatch 200B patch clamp amplifier (Molecular Devices, Sunnyvale, Calif.). Each chip was pre-checked to ensure a steady, low-noise baseline current and a linear current-voltage (I-V) curve that verified nanopore diameter using assessment buffer (1M NaCl, 10 mM Tris, 1 mM EDTA).

SS-Nanopore Analysis of HA

Prior to HA analysis, the assessment buffer was exchanged for measurement buffer to maximize signal-to-noise ratio. HA was loaded by pipetting 10-20 μl to one flow cell chamber at a final concentration of 50 ng/μl, unless otherwise noted. Data was collected at a rate of 200 kHz with a 100 kHz four-pole Bessel filter and analyzed using custom software, with which an additional 5 kHz low-pass filter was applied to all collected data. A given sample was tested in a series of trials at voltages ranging typically from 100-400 mV. Event threshold was defined as a deviation of at least five standard deviations from baseline current with a duration between 25 μs and 2.5 ms. Event Charge Deficit (ECD) was calculated for each deviation as the area encompassed by the event. Event rates were determined from uninterrupted current traces of 3.2 s increments at a single condition. The standard deviation measured between increments was used as an indication of measurement error.

EXAMPLE 3

Molecular Weight Discrimination with Quasi-Polydisperse HA

Figure 2A:
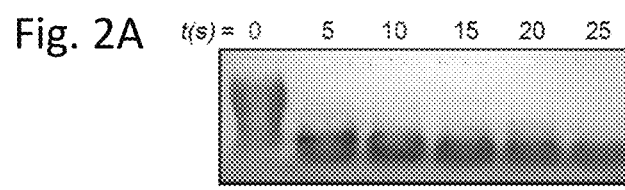
FIG. 2A is a gel image of polydisperse HA under increasing durations of exposure to a 175 W ultrasonic shearing bath, demonstrating increasing fragmentation.
Figure 2B:
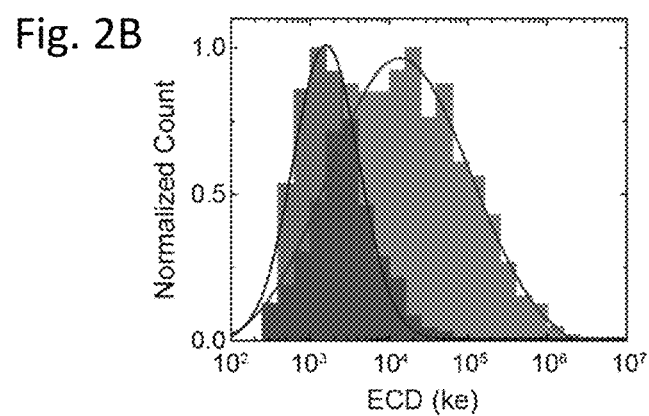
FIG. 2B are ECD histograms obtained from the 0 s (right) and 10 s (left) samples from FIG. 2A, showing a shifted mean with a reduced population width after shearing. Solid lines are Gaussian fits to the data.
Figure 2C:
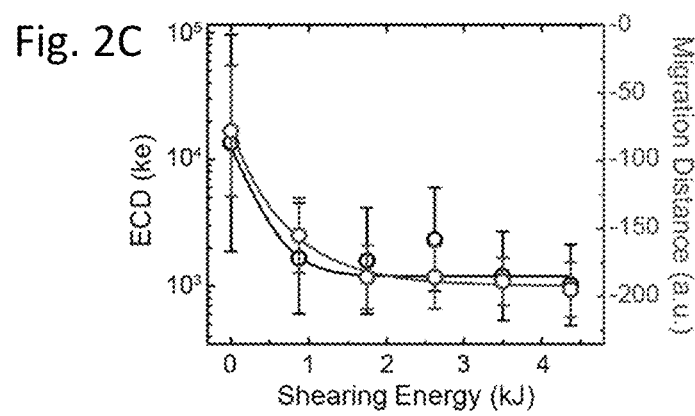
FIG. 2C illustrates the HA ECD (left) and gel migration distance (right) for all investigated shearing conditions, yielding nearly identical trends. Solid lines are exponential fits to the respective data.

A critical objective of the present disclosure is MW discrimination. As an initial test to demonstrate the ability of SS-nanopores to resolve differences in HA size, ultrasonic shearing was first used to fragment the same polydisperse material artificially. For this, separate aliquots of polydisperse HA were mechanically sheared using constant ultrasonication energy across a range of time durations, such that treated HA chains would be reduced in size to increasingly smaller chain lengths. The samples were first examined by agarose gel electrophoresis (FIG. 2a), showing both a reduced population width and a greater migration distance as shearing power was increased, thereby indicating narrowing distributions with smaller mean MW. The same material was subsequently measured by SS-nanopore. ECD distributions (FIG. 2b) for the untreated control, t(s)0, and a representative sheared sample (t=10 s, corresponding to ~1.8 kJ shearing energy) agreed qualitatively with gel observations, showing a narrower distribution and a clear shift towards lower ECD. Indeed, a comparison of ECD distributions with image analysis of the gel across shearing conditions demonstrated remarkable agreement between the two independent data sets (FIG. 2c), and suggested a straightforward correlation between HA MW and measured ECD from the SS-nanopore. In the present example, and others, Ultrasonic shearing of polydisperse HA and gel electrophoresis were prepared as described below.

Ultrasonic Shearing of Polydisperse HA

A 50 μl solution of polydisperse HA concentrate (1 μg/μl) was placed in a microTUBE AFA fiber snap-cap (Covaris, Woburn, Mass.) and mechanically sheared in a 7° C. water bath using a Covaris 5220 focused ultrasonicator (peak incident power of 175 W, 200 cycles per burst, 10% duty factor). Shearing was varied by increasing sonication times in 5 s increments. HA fragmentation was monitored by gel electrophoresis using the methods described below.

Gel Electrophoresis of HA

Electrophoresis was conducted on a 0.5% agarose gel in 1×TAE buffer. All samples (polydisperse and quasi-monodisperse HA) were aliquoted 12 μl volume in 0.15 NaCl solution with a minimum of 1-3 μg HA for visualization, consistent with previous literature. For synovial fluid samples, collected material centrifuged at 300×g for 5 minutes at 4° C. to pellet the cellular material, and the supernatant was retrieved and stored at −80° C. Prior to gel electrophoresis, the solution was thawed, diluted 1:20 in PBS buffer, and incubated with proteinase K (1 mg/mL) overnight to digest protein components. The resulting mixture was loaded directly onto gel because product visualization was insensitive to the trace background components. Electrophoresis (34 V, 3.5 hours at room temperature for polydisperse and quasi-monodisperse HA samples; 50 V, 8 hours at room temperature for synovial fluid HA samples) and detection (0.005% Stains-All (Sigma-Aldrich, St. Louis, Mo.) in 50% ethanol) were performed as described previously. Images were collected under white light transillumination using a ChemiDoc XRS+ system (BioRad, Hercules, Calif.) for FIGS. 2-3 and a VersaDoc system (BioRad) for FIG. 4. Migration distance was determined via image analysis (ImageJ) by determining the width and distance from the bottom of the loading well for each band.

EXAMPLE 4

Molecular Weight Discrimination with Quasi-Monodisperse HA

Figure 1C:
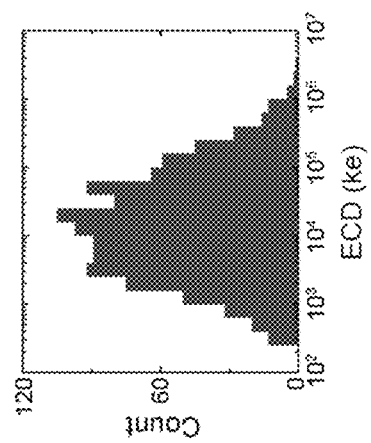
FIG. 1C illustrates a typical ECD histogram for polydisperse HA (n=1067) measured at 200 mV.
Figure 3A:
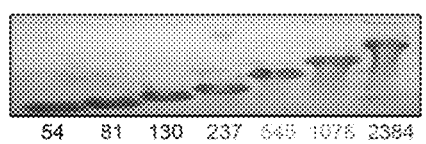
FIG. 3A is a gel image of quasi-monodisperse HA samples. Numbers beneath each lane represent the approximate molecular weight of the quasi-monodisperse HA sample in the lane.
Figure 3B:
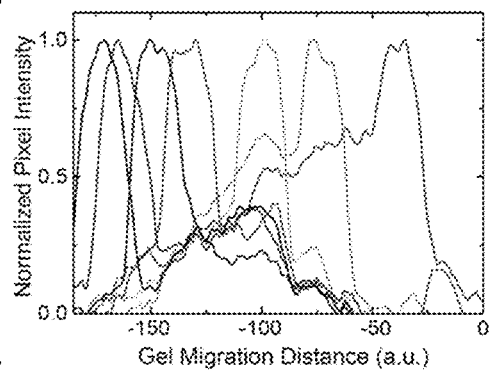
FIG. 3B is anormalized electropherogram of the gel image intensity for each MW sample shown in FIG. 3A. Shades match MW labels used in FIG. 3A.
Figure 3C:
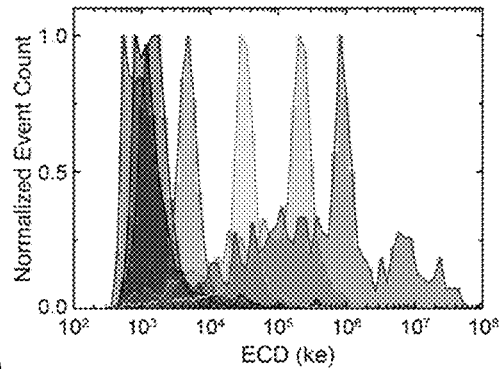
FIG. 3C is a collection of ECD histograms for each MW sample, with number of events considered: 54 (n=344), 81 (n=1031), 130 (n=3667), 237 (n=7835), 545 (n=5012), 1076 (n=1743), and 2384 kDa (n=640). Shades match MW labels used in FIG. 3A.

Having demonstrated HA detection with SS-nanopores with an initial validation of the size dependence of the approach, MW discrimination was pursued next by examining quasi-monodisperse HA. For this, discrete samples of HA ranging in MW from 54 kDa to 2.4 MDa were obtained. The production method for these materials took advantage of an established synthetic polymerization method to yield HA with narrow size distributions (typically ±5% of mean MW as received), as confirmed by gel electrophoresis (FIG. 3a). Each lane is marked according to the mean MW of the quadi-monodispersed HA in the lane. Lane intensity analysis (FIG. 3b) showed discrete populations for the set of quasi-monodispersed HA, demonstrating the experimental precision achievable by gel. Similarly, a series of defined peaks in the measured ECD (FIG. 3c) was observed upon probing the same materials individually by SS-nanopore. The population for each quasi-monodisperse peak was considerably narrower than that measured for polydisperse HA (c.f. FIG. 1c). Indeed, this narrowness suggested a higher resolution for the nanopore sensor than for gel analysis. It was found that ECD peak separations reduced for lower MW samples, but were distinguishable down to, as least, ~80 kDa. In some embodiments, ECD peak separations are distinguishable down to ~50 kDa or less. ECD peak separations can also be resolved down glycan monomer units, in some embodiments. For the largest samples (1.1 and 2.4 MDa), some low ECD background signal was observed that was attributed to fragmentation during handling or storage. Notably, a similar background was also visible on gel in the form of a smear in those two lanes (see FIG. 3a), further supporting the validity of the measurements.

Plotting the mean ECD for all quasi-monodisperse HA samples, a regular variation with respect to MW across voltages was observed (FIG. 3d) across nearly the entire investigated range by a power law fit with an average exponent of 2.35. Only the smallest sample (54 kDa) deviated significantly from this relationship, likely reflecting the minimum time resolution of the current electronics. It is expected that HA size differentiation at low MW ranges could be improved by one of ordinary skill in the art, for example, through the use of high bandwidth measurement techniques. The observed power law trend was similar to length dependences measured for other biopolymer translocation durations through SS-nanopores, and was again indicative of the impact of diffusion-limited kinetics. It was noted that the exponent recovered from the fit (2.15) was somewhat higher than previous reports for double-strand DNA, which ranged from 1.05-1.27. This difference may be attributed to increased diffusion facilitated by the more compact entropic conformation of HA and reduced self-avoidance, compared to double stranded DNA, in high ionic strength conditions. Regardless, establishment of this trend provides a critical conversion, enabling determination of HA MW at the single-molecule level from the direct electrical output of the SS-nanopore system, i.e. a conductance trace. For example, using the established MW to ECD relationship as a standard curve, the present disclosure enables estimation of a mean MW of the polydisperse HA sample. For instance, a mean MW in FIG. 1C can be estimated to be ~250 kDa.

EXAMPLE 5

SS-Nanopore Based Assessment of HA Extracted from Synovial Fluid

The analyses described in Examples 1-4 were next applied to HA in physiological fluids. The present Example focuses on synovial fluid where HA is the major viscoelastic component supporting joint lubrication and hydration, and its degradation has been implicated in joint disease. For example, a reduction in HA size and concentration has been associated with osteoarthritis (OA), a common joint pathology that leads to cartilage deterioration. Without intending to be bound by theory, it believed that the viscoelastic and immunomodulatory functions of HA are often size-dependent. This positions HA MW distribution, in particular, as a potentially valuable bioindicator of OA initiation, progression, and treatment efficacy. However, because of the non-selective nature of SS-nanopore signals (i.e. any translocating macromolecule can produce an event), it was not possible to probe synovial fluid without processing to remove other spurious components of biological origin. Therefore, a procedure (FIG. 4a) for HA isolation taking advantage of the high binding specificity of the versican protein G1 domain for HA was implemented.

In this procedure, a broad-spectrum protease was first used to digest protein components of physiological fluid (i), including lubricin, collagenases, and especially endogenous HA-binding proteins that could otherwise be retained in the collection scheme. Next, remaining protein (including the protease) and lipid components were removed by liquid-liquid phase extraction (ii), leaving in solution HA and other aqueous components like sulfated GAGs. The processed mixture was then incubated with the versican G1 domain immobilized on superparamagnetic beads, followed by magnetic isolation and washing of excess material (iii). Finally, bound HA was eluted from the beads thermally (iv) to yield a sample suitable for subsequent SS-nanopore analysis. The full protocol typically produced ~150 ng of high-purity HA from 50 µl of raw synovial fluid.

To test the feasibility and diagnostic potential of the SS-nanopore system, this HA isolation protocol was applied to synovial fluid bio specimens from an established equine model of post-traumatic OA (see Materials and Methods for details). For an initial demonstration of translational SS-nanopore analysis, two horses were employed. For the first (H1), conventional gel analysis (FIG. 4b&c, insets) showed a shift in the HA population toward lower MW 5 days after surgical carpal chip induction of OA. This shift is generally indicative of HA degradation, accumulation of low MW HA fragments, and disease progression, all of which are commonly observed in post-traumatic OA. Size distributions obtained by direct conversion of SS-nanopore ECD measurements to MW for the same samples also showed a notable shift in the same direction (FIG. 4b&c), with greater resolution at the lower MW range (<500 kDa) as compared to gels.

A second subject (H2) demonstrated an opposite shift towards larger MW after post-traumatic OA induction, as determined by gel analysis (FIG. 4d&e, insets). While OA is known to typically reduce mean HA size through joint friction shearing, this effect can in principle be overshadowed by an upregulation of HA synthesis pathways during the acute post-traumatic phase or be affected by natural HA turnover to produce a net increase in MW. This provided an experimental counterpoint for our SS-nanopore validation. Indeed, from SS-nanopore size distribution analysis of H2 (FIG. 4d&e), a notable shift was observed toward higher MW HA 12 days after surgical induction of post-traumatic OA, verifying the results from gel electrophoresis.

Figure 3D:
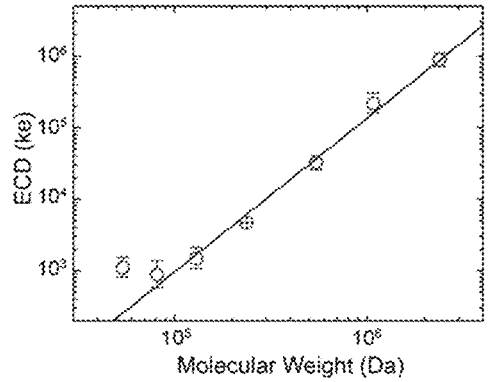
FIG. 3D illustrates the relationship between ECD measured by SS-nanopore and HA MW. Solid line is a power-law fit ($\alpha$=2.15) to the data down to 81 kDa.

It was found that the size distributions obtained for sham knees were not significantly different from day 0 to day 5 or 12, or compared to each other (FIG. 4b&d). This illustrates the consistency of the measurement across samples and devices. It is noted that, due to the size resolution of SS-nanopore analysis (c.f. FIG. 3d), it is possible that these distribution results overestimate the lowest MW HA in the detectable range and may miss extremely low MW molecules entirely. This limitation can be improved in future iterations of the system. However, the collective data from the two equine synovial fluid samples presented here are compelling demonstrations of the efficacy of the approach for translational size analysis of HA from biological specimens.

Figure 5:
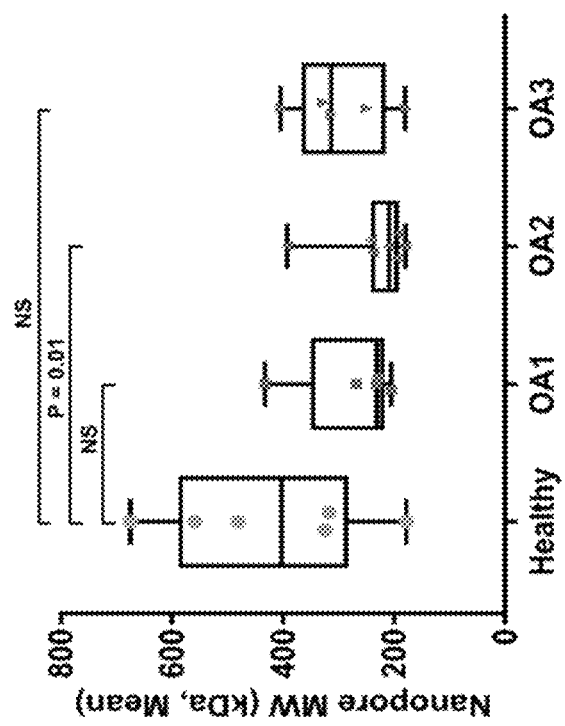
FIG. 5 illustrates a comparison of the mean molecular weight from distributions for HA extracted from individual horses radiographically determined to be healthy or have naturally developed osteoarthritis grade 1, 2 or 3, OA grade 3 being the most severe.

In addition, an analysis of three independent cohorts representing varying clinical grades of osteoarthritis was performed. Specifically, equine subjects having naturally developed osteoarthritis, as opposed to induced OA as previously described, were clinically assessed via radiographic pathology for severity in disease. Subjects were graded on a three step scale of severity of osteoarthritis grade 1, grade 2, and grade 3, wherein osteoarthritis grade 3 was considered the most severely diseased. Each cohort included at least 6 subjects, and a synovial fluid sample from each subject was collected, purified, and analyzed via SS-nanopore, as described above for FIG. 4. FIG. 5 represents a box and whisker plot of the mean molecular weight of glycosaminoglycan for each cohort of healthy or naturally occurring osteoarthritis. A statistically significant difference was identified between the healthy cohort and the osteoarthritis grade 2 cohort, suggesting the SS-nanopore can discriminate varying severity of osteoarthritis disease progression based on the mean molecular weight determined from the molecular weight distribution of the sample or subject.

A new SS-nanopore approach for the assessment of HA has been described, an emerging biomarker with relevance to a broad range of diseases. Through analysis of translocation event properties, HA MW can be determined on a per molecule basis, eventually yielding overall size distribution from only a few hundred or thousand individual molecules. After showing that the platform could detect HA and demonstrating a general capacity to distinguish broad changes in its size distribution, a consistent dependence of event ECD on HA MW using controlled quasi-monodisperse samples was measured. Finally, a general upstream isolation protocol was developed for the specific isolation of HA from biological fluids towards the purpose of SS-nanopore HA size distribution determination in synovial fluid from an equine post-traumatic OA model. Such a sample in this prototype device consisted of as little as 10 ng of HA in a 10 µl volume, which could be measured electrically in ~2 hrs. This time could be shortened significantly by using higher concentrations.

This study is the first to establish SS-nanopores as a tool for the analysis of HA, demonstrating high quality, reliable, and reproducible quantitative data on both HA detection and size distribution determination from biological specimens. The sensitivity, speed, and small sample volume requirements of this approach make it attractive as the basis for future diagnostic tools with distinct advantages over conventional technologies. Applications for the technology may include both translational measurement of HA as a biomarker, as well as assessment of HA synthesis products for commercial or research purposes. The results also suggest a wider role for the measurement platform in assessing other important GAGs that may have additional importance as bioindicators of diverse pathologies, including heparan sulfate, chondroitin sulfate and keratan sulfate.

In the present Example, and others, the equine model of induced osteoarthritis and high purity HA extraction methods from synovial fluid collected from the equine subjects were performed as described below.

Equine Model of Osteoarthritis

Equine synovial fluid was obtained from adult horses (2-5 years old) with radiographically normal carpal joints. Post-traumatic osteoarthritis was induced surgically through a carpal chip defect in one randomly assigned forelimb. Briefly, an 8 mm osteochondral fragment was created in the dorsal rim of the radial carpal bone and left within the joint. The exposed subchondral bone was then debrided using an arthroburr to generate a 15 mm defect. The debris generated from the procedure was not removed from the synovial cavity. A sham arthroscopic operation (i.e. no chip) was performed on the contralateral leg to serve as a control. Two weeks after the induced osteochondral fragmentation, without operative intervention, the horses were subjected to a 30 min treadmill/5 days per week training regimen to initiate osteoarthritis (OA), and synovial fluid samples were collected from both joints on day 0 as well as 5 (H1) or 12 (H2) days post-surgery. Samples were kept at −80° C. prior to use. All animal and tissue harvesting protocols were approved by Cornell University's Institutional Animal Care and Use Committee (Protocol Number: 2012-0097).

High Purity HA Extraction from Synovial Fluid

HA was isolated from the equine synovial fluid using a protocol adapted from Yuan et al. 50 µl raw equine synovial fluid was first incubated with 1.8 U/mL proteinase K (New England Biolabs, Ipswich, Mass.) for 15 min at 37° C. to digest protein components, including those with HA-binding capacity, followed by heat treatment at 95° C. for 15 min to inactivate proteinase K and further denature remaining components. An equal volume of a phenol:chloroform:isoamyl alcohol (25:24:1 v/v, Fisher Scientific) was then added to the sample and mixed thoroughly before being centrifuged for 15 min at 14,000×g in a Phase Lock Gel Tube (QuantaBio, Beverly, Mass.) to separate the aqueous HA from the organic component. This extraction process was repeated once using pure chloroform to remove residual phenol from the aqueous phase, which was found to adversely affect downstream protein function.

For high purity isolation of HA, streptavidin magnetic beads (Dynabeads M-280, Invitrogen, Carlsbad, Calif.) at a concentration 10 mg/mL were washed three times in 1×PBS, 0.05% Tween by adding buffer, mixing gently, and aspirating under magnetic field, and then three times in 1×PBS only. After washing, 250 µl of beads were resuspended in 50 µl of 1×PBS. Then, 21 µl of biotinylated versican G1 domain (bVG1, 1.23 µg/µl, Echelon Biosciences, Salt Lake City, Utah) was then added directly to the beads and incubated for 1 hour at room temperature on a rocker. After incubation, the beads were washed three times with 150 µl 1×PBS to remove excess unbound bVG1.

The bVG1-streptavidin beads were subsequently reconstituted with the extracted HA isolate solution and incubated at room temperature for 24 hrs with gentle rocking. The sample was placed on a magnet to pull down the beads (with bound HA) and the supernatant was aspirated. The beads were washed three times with 1×PBS, after which deionized water was added to the sample to a final volume of 50 µl. To denature the bVG1 and release the bound HA, the sample was placed on a heating block at 95° C. for 15 min. Finally, the vial was placed on a magnet and the solution containing released, purified HA was removed and stored at −20° C. until use. Yield was determined through direct quantification of the isolate with an enzyme-linked immunosorbent assay kit (HA ELISA, Echelon Biosciences)

EXAMPLE 6

SS-Nanopore Analysis of Sulfated Glycosaminoglycans

The present Example illustrates SS-nanopore analysis of sulfated and non-sulfated glycosaminoglycans of varying types, which in some cases, can be used as a diagnostic tool or treatment for one or more pathologies, as described above. FIG. 6A illustrates an exemplary electrical conductance trace showing translocations of 6-O-sulfated heparosan and non-sulfated heparosan. Briefly, these synthetic glycans having a backbone of about 470 sugars (about 95 kDa) were analyzed by SS-nanopore using salt solution of 6 M LiCl. The ECD for each sample was then calculated, as described above, and plotted against the normalized event count. Results shown in FIG. 6B illustrate a clear shift in a lower mean ECD for sulfated-heparosan compared to non-sulfated heparosan. The shift suggests a direct correlation between the trace conductance signal and sulfation of the glycosaminoglycans, and demonstrates SS-nanopore-based discrimination between the two molecular groups.

Figure 7A:
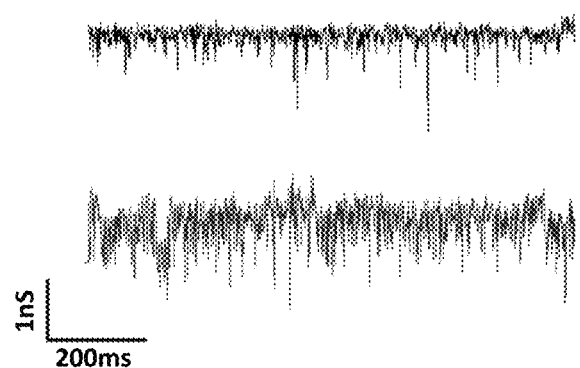
FIG. 7A illustrates typical conductance traces (6M LiCl) showing translocation events of sulfated HA (top) and quasi-monodisperse HA control (bottom), demonstrating high SNR analysis of sulfated and non-sulfated HA. Both synthetic HA samples have ~150 kDa backbones.
Figure 7B:
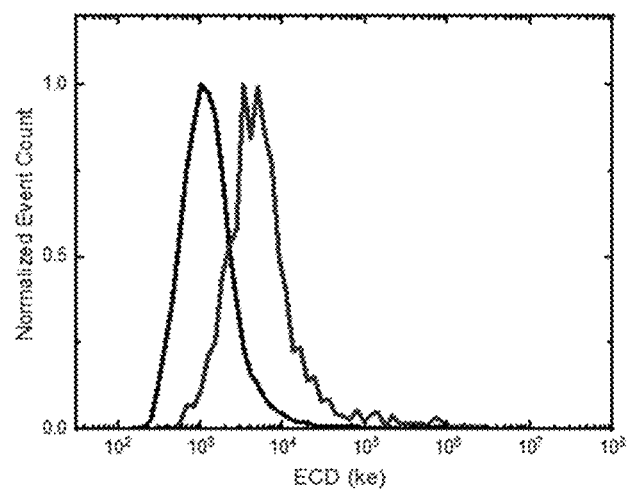
FIG. 7B illustrates normalized ECD distributions for sulfated HA (left) and a control quasi-monodisperse HA (right) sample. The shift suggests a direct correlation between signal and sulfation.
Figure 7C:
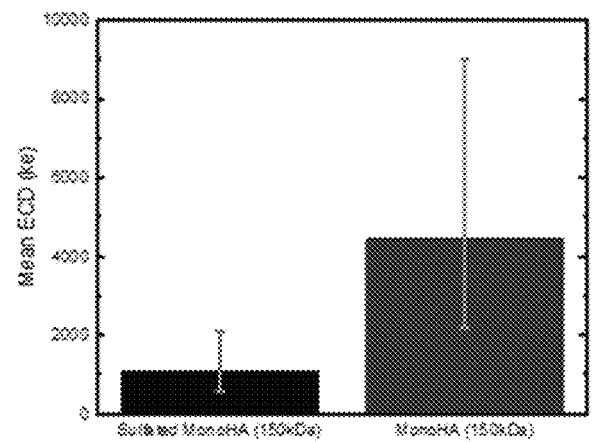
FIG. 7C is a bar graph comparison of mean ECD from distributions of sulfated and non-sulfated HA showing a statistical significant difference between the two.

Additionally, FIG. 7A illustrates an exemplary electrical conductance trace showing translocations of sulfated quasi-monodispersed HA (top) and non-sulfated quasi-monodispersed HA (bottom). Briefly, these synthetic glycan samples having a backbone of about 150 kDa were analyzed by SS-nanopore using salt solution of 6 M LiCl. The ECD for each sample was then calculated, as described above, and plotted against the normalized event count. Results shown in FIG. 7B illustrate a clear shift in a lower mean ECD for sulfated HA compared to non-sulfated HA. A graph plotting the mean ECD of each sample, shown in FIG. 7C, illustrates a statistically significant difference in the mean ECD between the sulfated and non-sulfated HA.

Overall, FIG. 6 and FIG. 7 demonstrate feasibility and enablement of differentiating sulfated glycosaminoglycans from non-sulfated glycosaminoglycans, including varying types of glycosaminoglycans, from a mixture of the two. Differences in the amount or level of sulfation of glycosaminoglycans can thus be differentiated, indicating compositional differences (i.e. each extra sulfate per disaccharide [e.g., a N—S or O—S] can add an additional −1 charge to the glycosaminoglycan chain).

EXAMPLE 7

SS-Nanopore Assessment of HA Isolated from Human Plasma

Figure 8A:
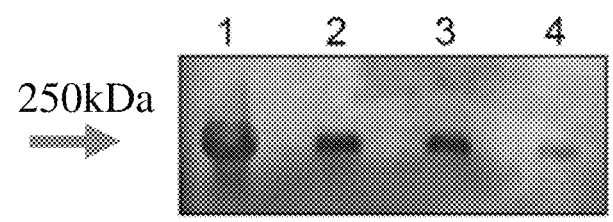
FIG. 8A is an agarose gel analysis of 237 kDa quasi-monodisperse HA spiked into and then isolated from plasma and analyzed at various steps during the isolation process. Lanes: (1) control sample of 250 kDa quasi-monodispersed HA; (2) phenol:chloroform extracted; (3) chloroform treated; (4) HA eluted from magnetic beads.

The analysis described in Example 5 was also applied to HA in another type of physiological fluid, which, in the present Example, was human plasma. To illustrate feasibility of isolating HA from other complex physiological fluid, samples of human plasma were spiked with quasi-monodispersed HA of about 250 kDa and isolation methods as in Example 5 hereinabove were performed. FIG. 8A is an image of an agarose gel electrophoresis of the HA after subsequent steps of the isolation protocol according to Example 5. Each of lanes 2-4 represents the HA isolated from the spiked sample following each step of the isolation protocol. Lane 1 is a control sample of 250 kDa quasi-monodisperse HA. Lane 2 is a sample of 250 kDa HA extracted from spiked human plasma after a phenol:chloroform extraction step. Lane 3 is a sample of 250 kDa HA extracted from spiked human plasma following the same treatments as in lane 2 and chloroform treated. Lane 4 is a sample of 250 kDa HA extracted from spiked human plasma following the same treatments as in lane 3 and eluted from magnetic beads. Lane 4 clearly demonstrates a successful isolation of HA from a complex physiological fluid, such as human plasma.

Figure 8B:
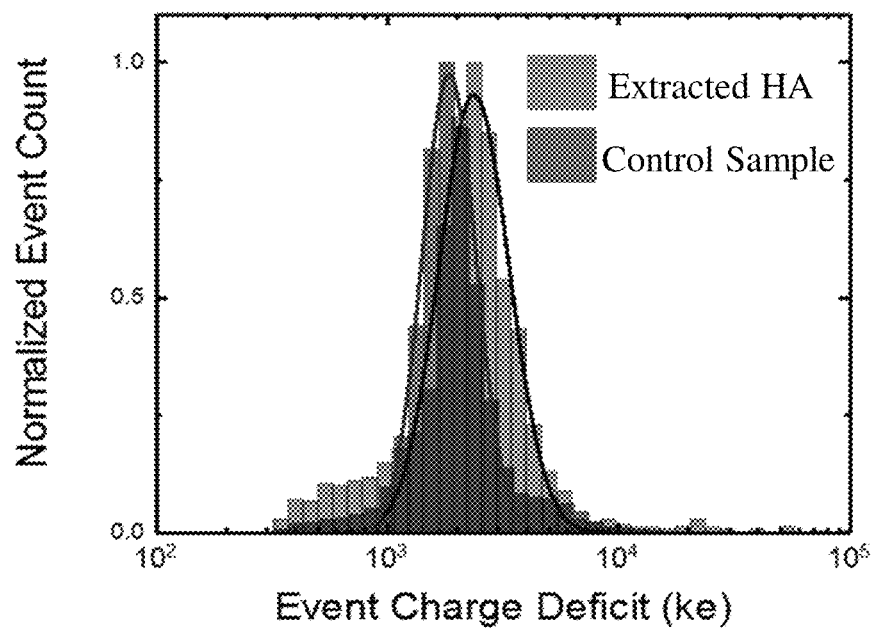
FIG. 8B is a nanopore analysis of isolated 250 kDa quasi-monodispersed HA material from lane 1 (left) and lane 4 (right) of FIG. 8A.
Figure 8C:
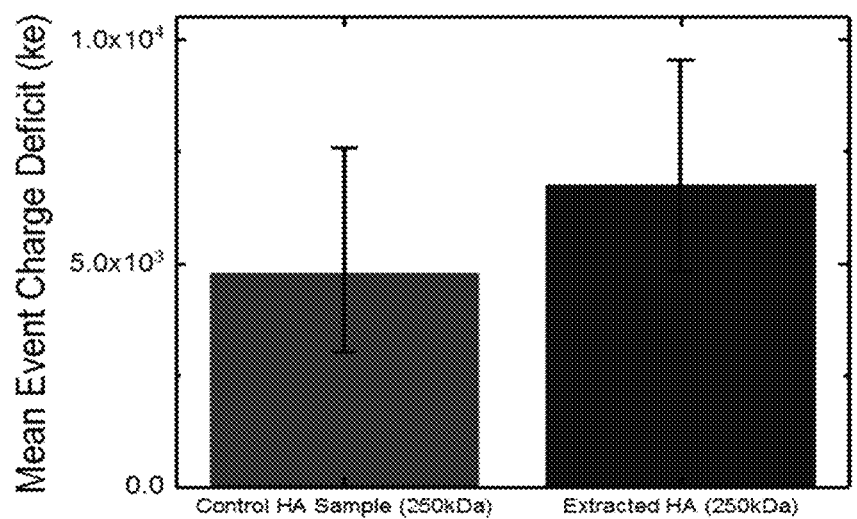
FIG. 8C is a graph of the mean ECD signal for each sample shown in FIG. 8B, which shows no significant difference between the two samples.

The isolated HA was then subjected to SS-nanopore analysis and compared to SS-nanopore analysis of the control quasi-monodispersed HA. Results shown in FIG. 8B show the mean ECD for the control HA (left) and the isolated HA (right), which was then plotted against the normalized event count in FIG. 8C. No significant difference was observed between the control HA sample and isolated HA from the spiked sample, demonstrating the ability to isolate HA, as shown, and agreement between the two samples in their respective SS-nanopore measurements.

EXAMPLE 8

Isolation and Quantification of HA from Specimen Having a Low Glycosaminoglycan Concentration and/or a High Native Salt Concentration The analysis described in Example 5 was also applied to HA in yet another type of physiological fluid, which in the present Example, was human urine. It is known that human urine has a relatively low glycosaminoglycan concentration and a high salt concentration. Other exemplary complex fluids can include, but are not limited to, sweat and tears. To illustrate feasibility of isolating HA from such a complex physiological fluid having a naturally high concentration of salt, samples of human urine were first subjected to a centrifugation protocol to concentrate the urine and the samples were rehydrated at a very high concentration. The samples were then subjected to dialysis to remove or minimize the native salts to avoid interference with the SS-nanopore analysis. The resulting dialyzed sample was then subjected to the extraction protocol, as described above in Example 5, followed by SS-nanopore analysis. The SS-nanopore ECD distribution of native HA extracted from 4 mL human urine is shown in the top panel of FIG. 9.

Figure 9:
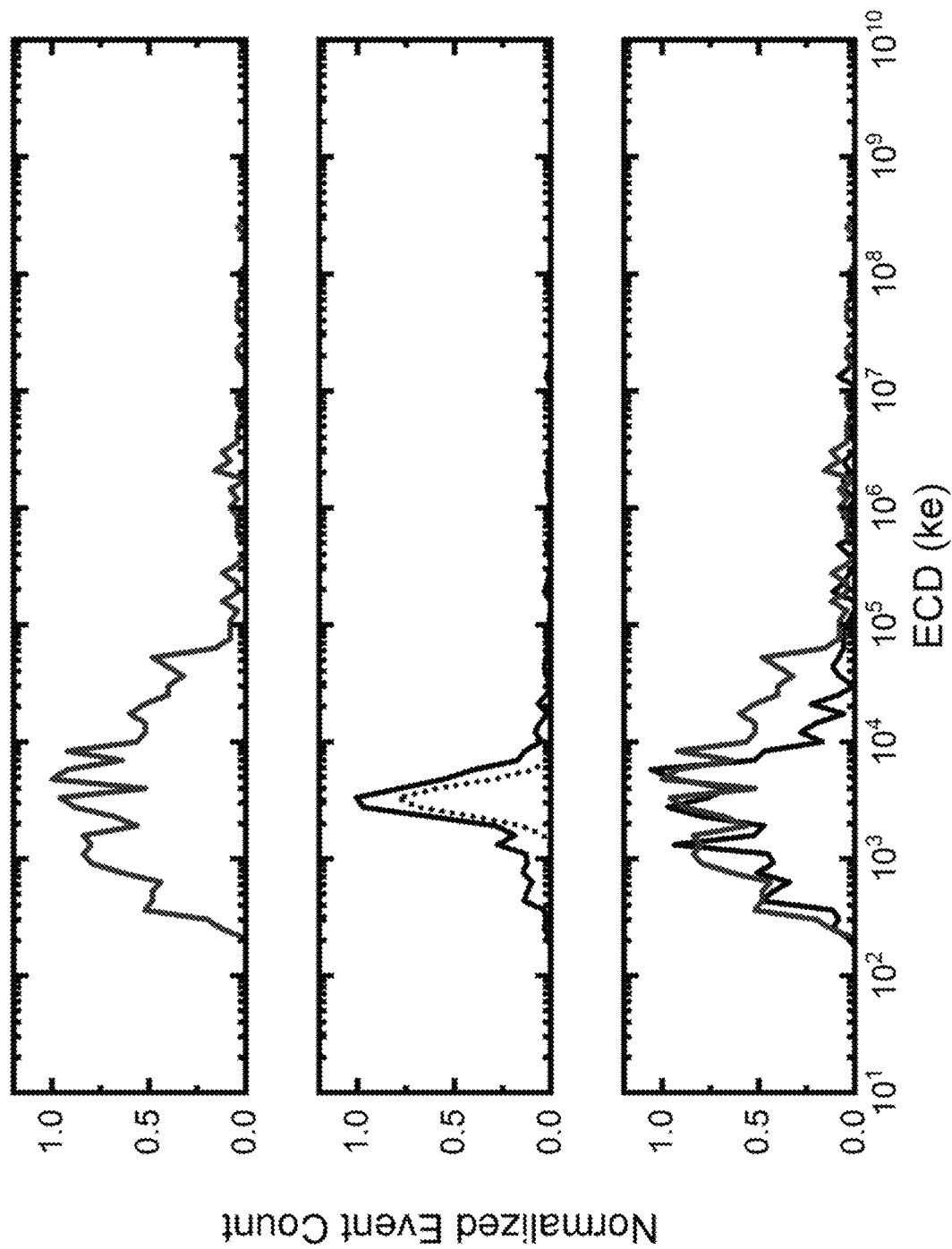
FIG. 9 (top panel) is a SS-nanopore ECD distribution of native HA extracted from 4 mL human urine (middle panel) a SS-nanopore ECD distribution measured for the same human urine biospecimen, but with a 150 kDa quasi-monodisperse spike-in. The dashed line is a Gaussian fit representing the spike-in contribution alone; and (bottom panel) a subtraction of the spike-in contribution yields an apparent native distribution (black) that closely resembles the unspiked native distribution (gray overlay from top panel).

In order to identify the corresponding MW and concentration from the ECD distribution, the same urine specimen was spiked with 150 kDa quasi-monodisperse HA and analyzed by SS-nanopore, as shown by the solid line in the middle panel of FIG. 9. The dashed line of the middle panel represents a Gaussian fit representation of the ECD of only the spiked-in HA sample. The spike-in contribution of the ECD was then subtracted out of the analysis, which yielded a native distribution, shown as the black line of the bottom panel in FIG. 9. As shown in the bottom panel of FIG. 9, the spiked-in sample having the spike subtracted closely resembles the distribution of the native, unspiked distribution, overlaid and shown as the gray line in the bottom panel of FIG. 9. The known spike-in can then be used to determine the concentration of the native HA, which in the present example is 46 ng/mL.

EXAMPLE 9

SS-Nanopore Analysis of HA Isolated from Bronchial Lavage Specimens

Figure 10A:
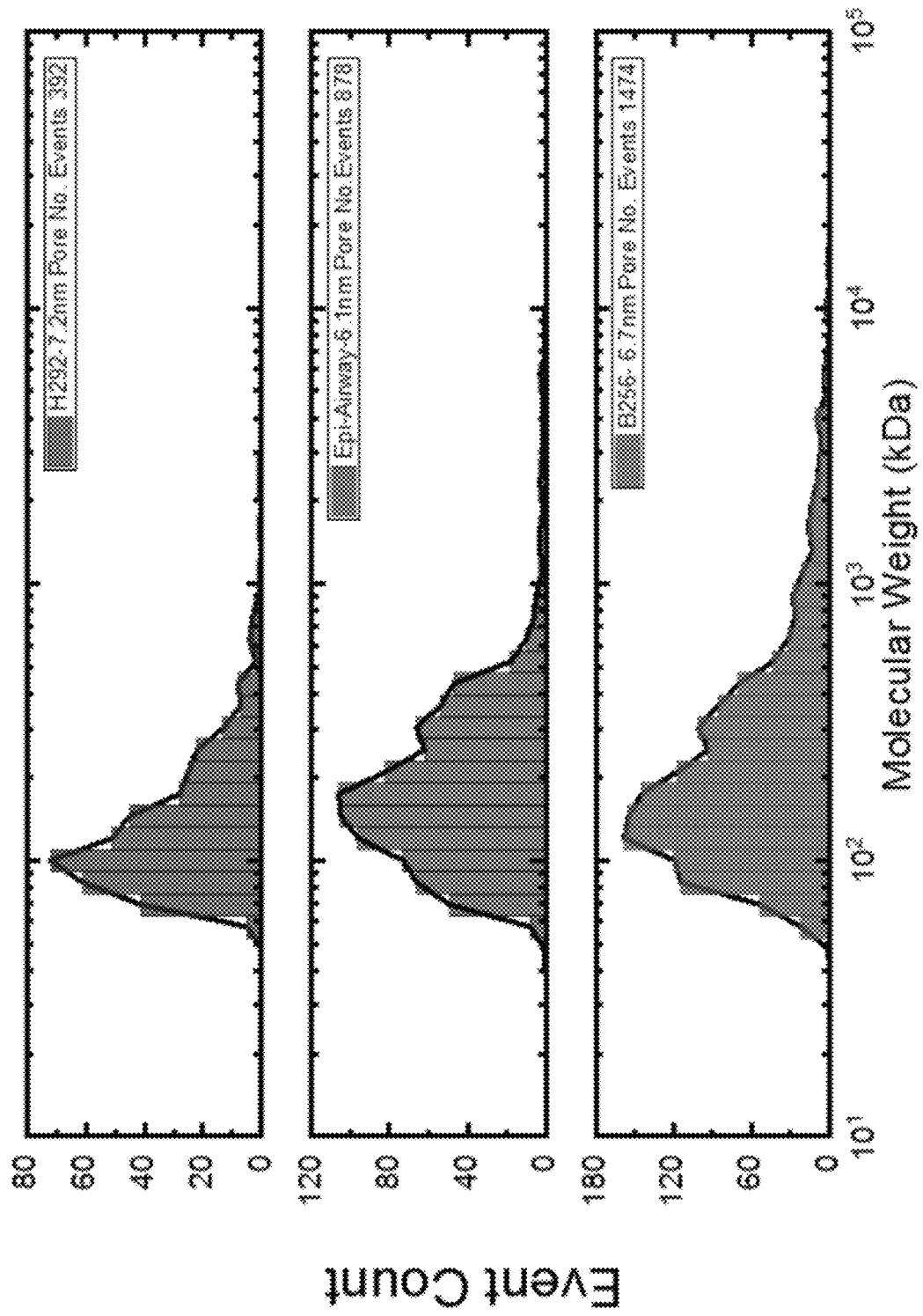
FIG. 10A illustrates molecular weight distributions for three example bronchial lavage bio specimens.
Figure 10B:
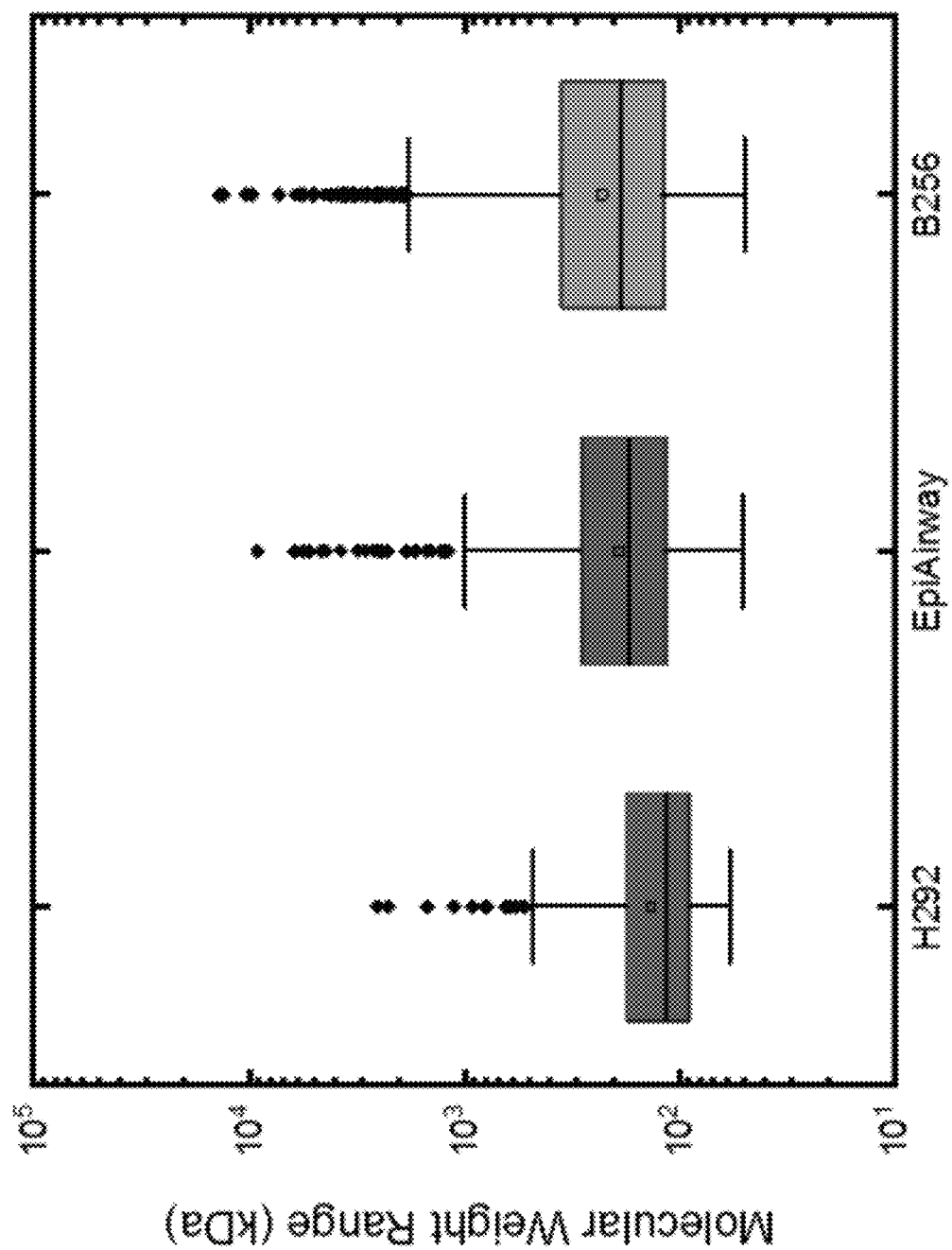
FIG. 10B illustrates the mean molecular weight with standard deviation error for the same samples as in FIG. 10A.

The analysis described in Example 5 was also applied to HA isolated from another type of physiological fluid, which in the present Example, was bronchial lavage. Biospecimen from three exemplary bronchial lavage models were collected and subjected to the isolation protocol and SS-nanopore analysis, as described above. FIG. 10A illustrates the molecular weight distribution derived from the SS-nanopore analysis of each exemplary model. FIG. 10B illustrates the mean molecular weight for a cohort of samples collected from each exemplary bronchial lavage model. As expected, the mean molecular weight across the three bronchial lavage models did not significantly differ, suggesting a reliable measurement across different samples of the same bio specimen type. Accordingly, the present example demonstrates a consistency that, in some embodiments, can be expected across patient samples of the same biospecimen type or of the same tissue origin.

EXAMPLE 10

SS-Nanopore Analysis of Fabricated HA

Figure 11A:
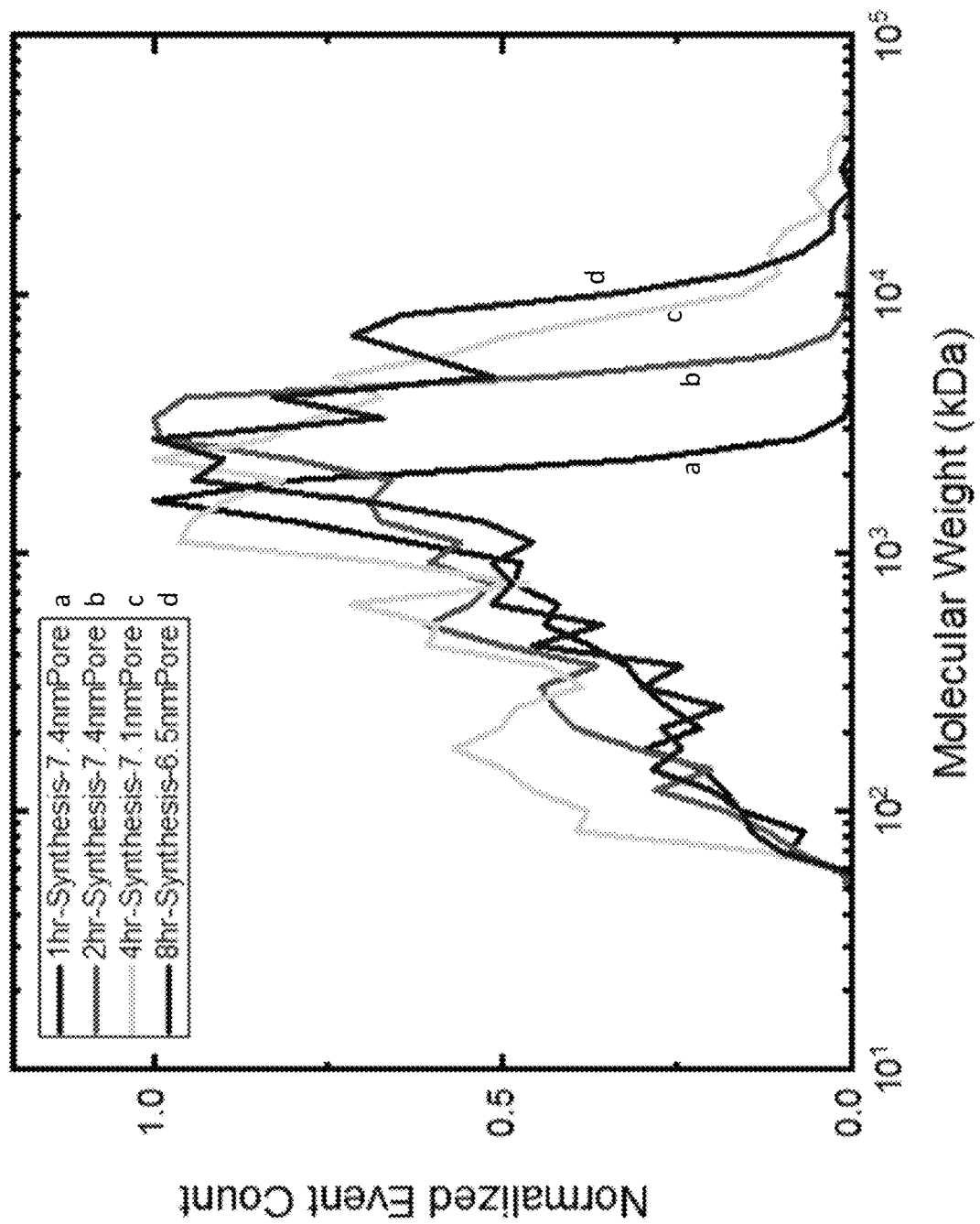
FIG. 11A illustrates molecular weight distributions obtained by SS-nanopore using HA material generated using hyaluronan synthase enzymes incubated for 1 hour (a), 2 hours (b), 4 hours (c), and 8 hours (d).
Figure 11B:
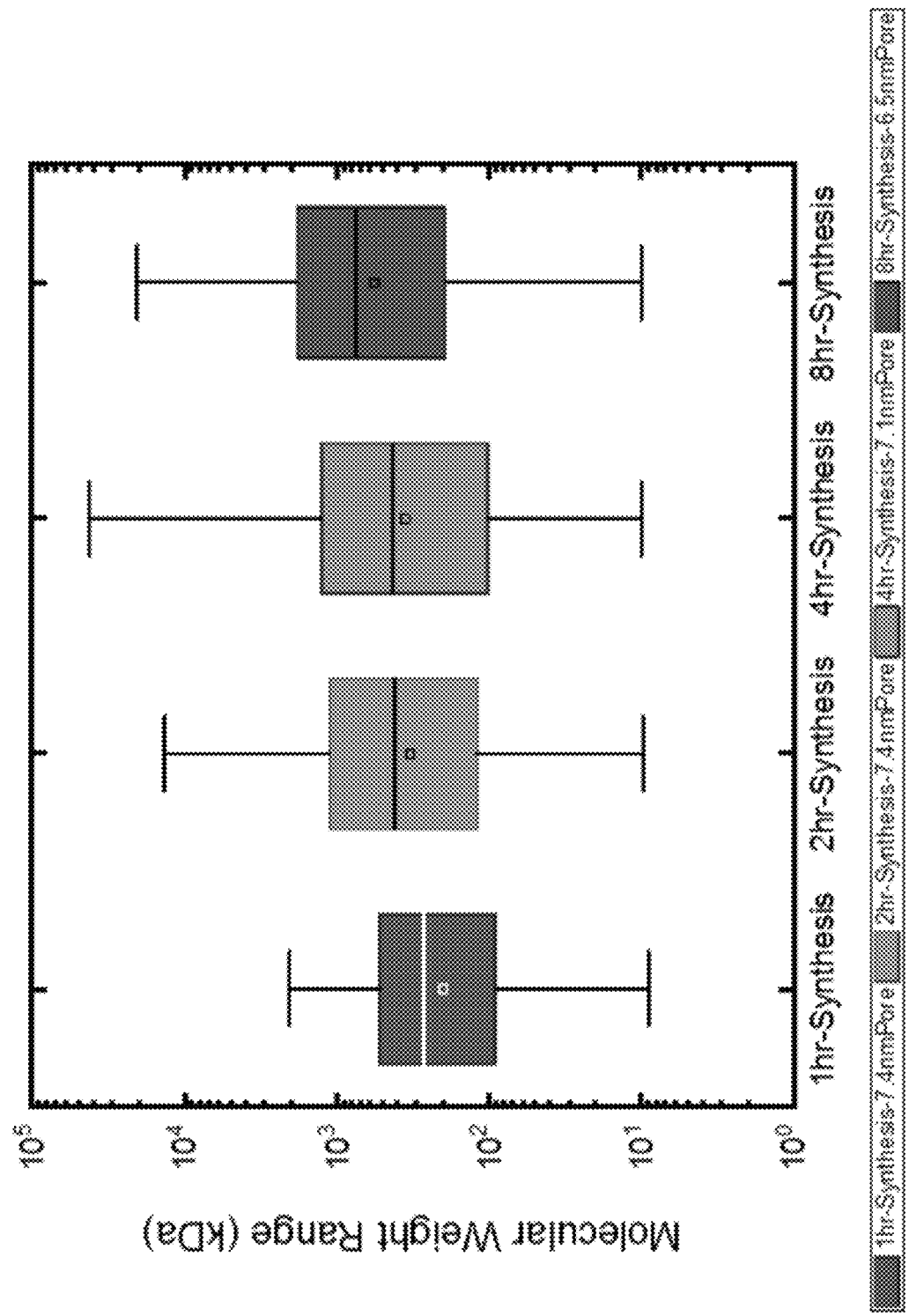
FIG. 11B illustrates statistical analyses of FIG. 11A showing that the mean MW and MW range (window) each generally increase with incubation time of the synthase enzymes.

The present Example demonstrates discrimination of HA size using SS-nanopore analysis. Specifically, HA of increasing length were fabricated using bacterial derived hyaluronan synthase enzyme, as described hereinabove. The enzyme was incubated for increasing periods of time: 1 hr (a), 2 hr (b), 4 hr (c), or 8 hr (d). The longer the incubation time, the longer the HA molecules generated by the enzyme. The synthetic HA sample representing each incubation time period was then analyzed by SS-nanopore. As shown in FIG. 11A, the longer the incubation time, the greater the shift in the molecular weight distribution toward a higher molecular weight distribution profile. Additionally, as expected, a statistical analysis of the same synthetic samples showed a similar trend of increasing mean molecular weight and molecular weight range as the incubation time increased, as shown in FIG. 11B.

EXAMPLE 11

SS-Nanopore Calibration

Figure 12:
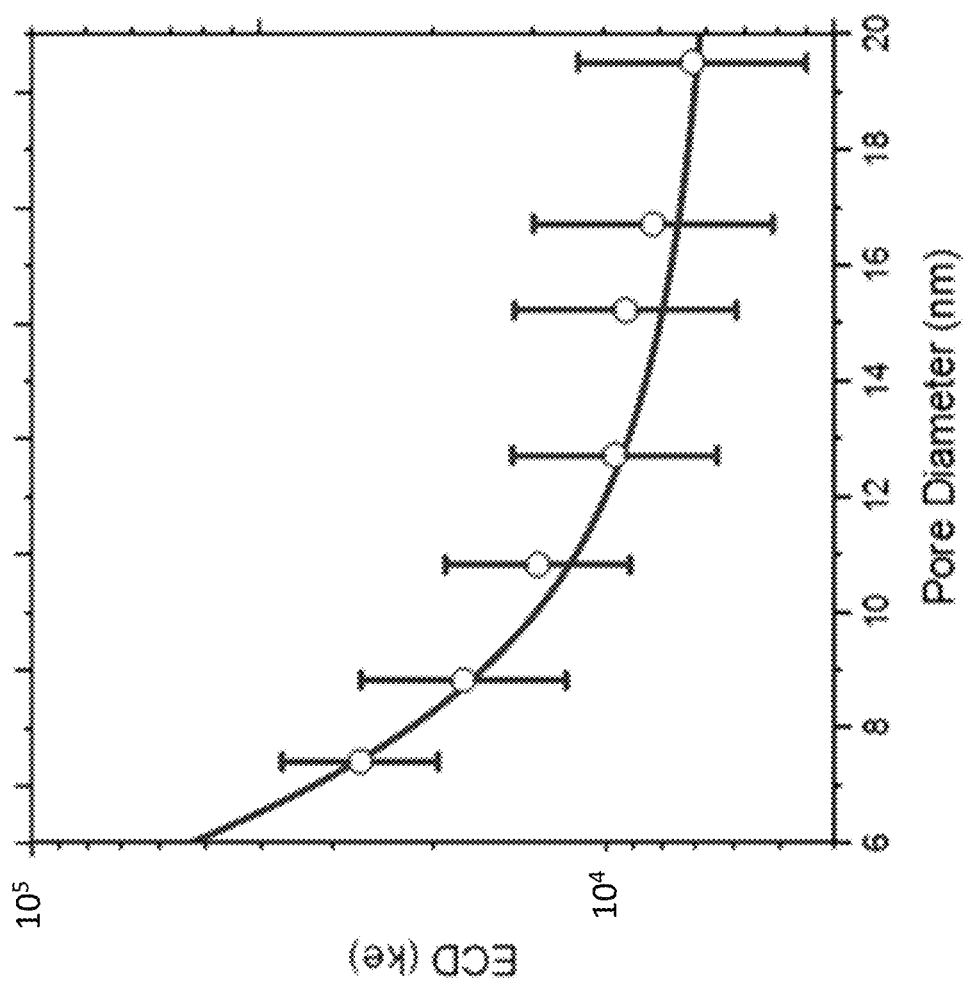
FIG. 12 illustrates mean ECD (error bars are standard deviation) obtained by SS-nanopore from a single molecular weight of quasi-monodisperse HA (150 kDa) measured on nanopore devices with varying diameters.

The present Example illustrates SS-nanopore diameter dependence while recording data of glycosaminoglycan translocation events through the nanopore. Samples of quasi-monodisperse HA of about 150 kDa were measured using SS-nanopores of varying diameter between 6 nm and 20 nm. As described above, the mean ECD was calculated for each size nanopore. Results shown in FIG. 12 demonstrate that the mean ECD exhibits a nanopore size-dependence such that as the nanopore diameter decreases the ECD increase. Therefore, in some embodiments, the nanopore diameter should be accounted for when determining a molecular weight distribution of a composition from the recorded data. Specifically, in some cases, a calibration curve can be used wherein a background conductance trace of a known sample of known molecular weight can be translocated through the nanopore to calibrate for variation in nanopore diameter prior to translocating a mixture, particularly since even a 1 nm difference in nanopore diameter can influence the ECD calculation and resultant molecular weight distribution.

EXAMPLE 12

SS-Nanopore Analysis of HA-Protein Interactions

Figure 13:
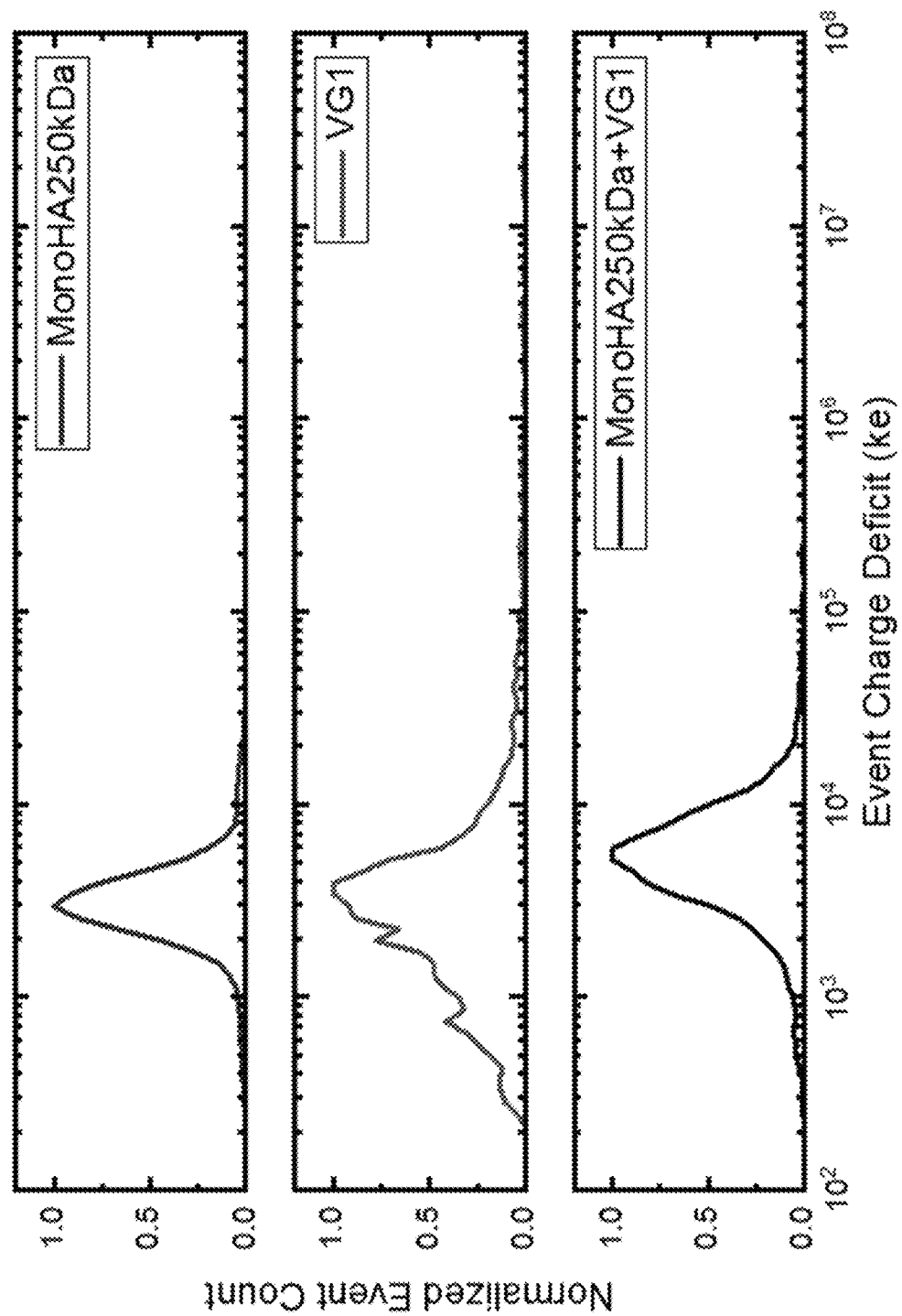
FIG. 13 illustrates (top panel) ECD distributions obtained from SS-nanopore from a single molecular weight of quasi-monodisperse HA (250 kDa); (middle panel) ECD distributions obtained from SS-nanopore from Versican G1 domain (VG1); and (bottom panel) ECD distributions obtained from SS-nanopore from incubating the quasi-monodisperse HA and VG1 together. Measurements were taken using 6MLiCl buffer.

The present example illustrates SS-nanopore analysis of glycosaminoglycan-protein interactions. Briefly, ECD distributions of quasi-monodispersed HA of about 250 kDa (MonoHA250 kDa) and versican G1 domain protein (VG1) were determined. MonoHA250 kDa and VG1 were then incubated together to allow binding, and an ECD distribution was determined for MonoHA250 kDa+VG1 complexes. Measurements were performed under 6 M LiCl buffer conditions. Results shown in FIG. 13 suggest discernable differences in glycosaminoglycan-protein interactions can be detected using SS-nanopore analysis. Furthermore, as described below in Example 12, modification of salt concentrations, which can influence the strength of glycosaminoglycan-protein interactions and the trace conductance of SS-nanopore analysis, can enhance the SS-nanopore based discrimination of glycosaminoglycan-protein interactions.

It should be understood that the present example is merely illustrative of the ability to characterize glycosaminoglycan-protein interactions using a SS-nanopore, as described herein. Not intending to be bound by theory, it is believed that a more physiologically relevant salt concentration, such as 150 mM, will allow glycosaminoglycan-protein interactions present in bio specimens (e.g., derived from bodily fluids, tissue samples) to be maintained, and consequently influence the ECD distribution of the complex. Accordingly, the present example can use varying salt conditions, such as varying salt concentrations, to enhance both the glycosaminoglycan-protein complex stability and the SS-nanopore discrimination of glycosaminoglycan-protein complexes.

EXAMPLE 13

SS-Nanopore Analysis Using Varying Salt Conditions

Figure 14B:
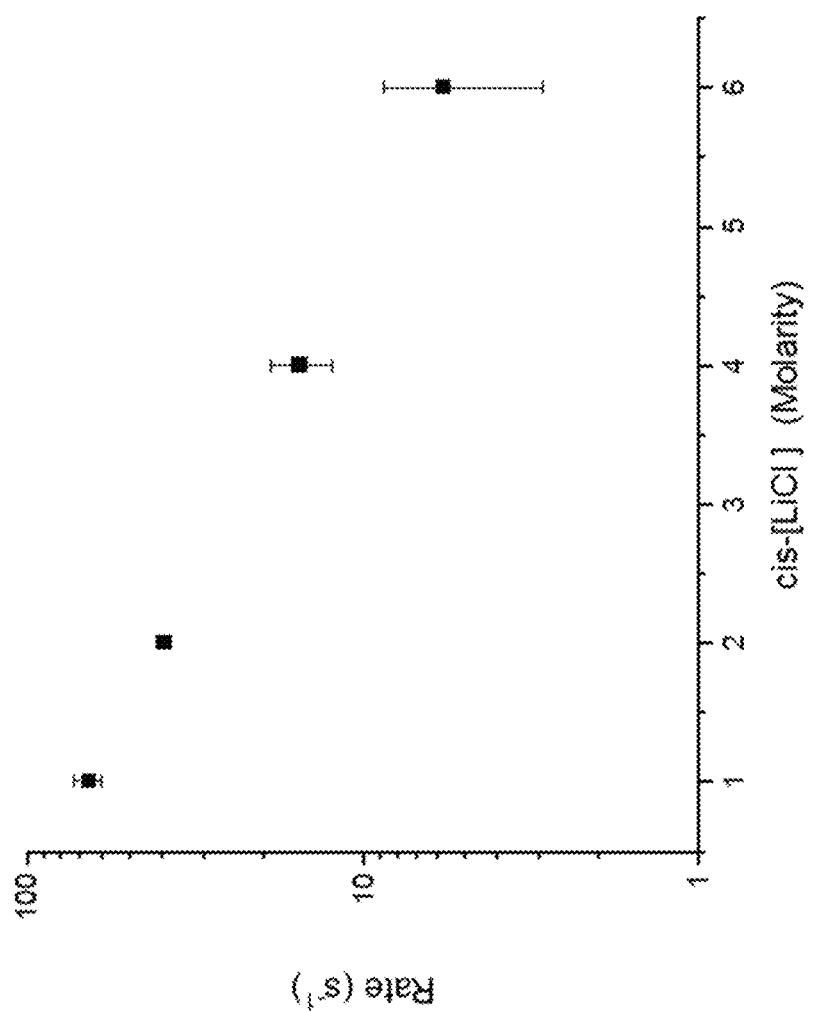
FIG. 14B illustrates the rate of translocation events as a function of cis-LiCl concentration.
Figure 14C:
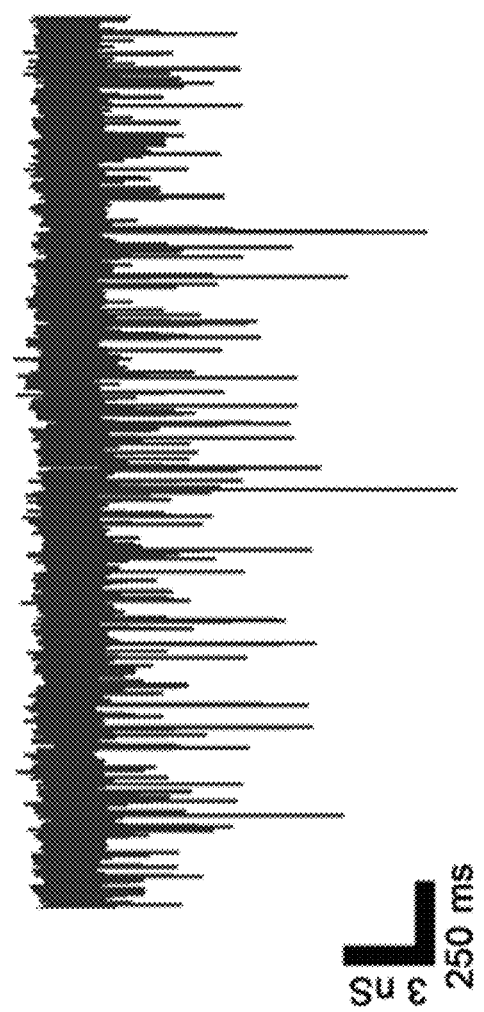
FIG. 14C illustrates an exemplary SS-nanopore conductance trace for 1 ng/uL polydisperse HA under asymmetric salt measurements of 150 mM:6 M (cis:trans) salt concentration.

The present example illustrates how varying the salt concentration during SS-nanopore analysis can affect the SS-nanopore sensitivity of the rate of translocation events. Briefly, polydisperse HA at a constant concentration (3 ng/uL) was analyzed, as described in Example 2, while the salt concentration of the cis chamber was decreased from 6 M to 4 M, 2 M, 1 M or 150 mM LiCl, and the trans chamber remained constant at 6 M LiCl. An electrical conductance trace was recorded for each condition at a 200 mV applied voltage. As shown in FIG. 14A, a more sensitive quantification is observed as the salt concentration of the cis chamber decreases. FIG. 14B demonstrates that the measured translocation event rate plotted as a function of the cis LiCl concentration exhibits a power law relationship as the cis-LiCl concentration increases. Overall, these results suggest that the sensitivity of SS-nanopore can be modified by increasing or decreasing the salt concentration of the cis and/or trans chamber. Specifically, these results suggest that the sensitivity of the SS-nanopore can be increased by decreasing the cis-LiCl concentration.

Various embodiments of the invention have been described in fulfillment of the various objects of the invention. It should be recognized that these embodiments are merely illustrative of the principles of the present invention. Numerous modifications and adaptations will be readily apparent to those skilled in the art without departing from the spirit and scope of the invention.

The invention claimed is:
1. A method of biomolecular analysis comprising:
providing a mixture comprising glycosaminoglycans and proteins;
contacting the mixture with a membrane comprising at least one nanopore;
applying an electric field across the nanopore;
recording data of biomolecular translocation events through the nanopore; and
deriving glycosaminoglycan-protein interactions from the data, wherein the glycosaminoglycan-protein interactions include glycosaminoglycan-protein binding.
2. The method of claim 1, wherein the data comprises dwell time of glycosaminoglycan-protein complexes in the nanopore or translocation event depth of glycosaminoglycan-protein complexes.

3. The method of claim 1, wherein the data comprises dwell time of glycosaminoglycan-protein complexes in the nanopore and translocation event depth of the glycosaminoglycan-protein complexes.

4. A method of biomolecular analysis comprising:
providing a mixture comprising glycosaminoglycans and proteins;
contacting the mixture with a membrane comprising at least one nanopore;
applying an electric field across the nanopore;
recording data of biomolecular translocation events through the nanopore; and
deriving glycosaminoglycan-protein interactions from the data, wherein the data comprises dwell time of glycosaminoglycan-protein complexes in the nanopore and translocation event depth of the glycosaminoglycan-protein complexes.

* * * * *